(12) United States Patent
Glasgow et al.

(10) Patent No.: US 6,620,144 B1
(45) Date of Patent: Sep. 16, 2003

(54) COMPOUND NAPKIN

(75) Inventors: Tara Glasgow, New Hope, PA (US); Kendra S. Rose, Lawrenceville, NJ (US); Michele Mancuso, Raritan, NJ (US); John Ulman, Woodbridge, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/436,484

(22) Filed: Nov. 8, 1999

(51) Int. Cl.⁷ ................................................ A61F 13/15
(52) U.S. Cl. ............................. 604/385.17; 604/385.01
(58) Field of Search ........................... 604/385.01, 380, 604/385.21, 378, 371, 385.17

(56) References Cited

U.S. PATENT DOCUMENTS

| | | | | |
|---|---|---|---|---|
| 2,295,016 A | 9/1942 | Scribner | ...................... | 128/290 |
| 2,331,355 A | 10/1943 | Strongson | ................... | 128/290 |

(List continued on next page.)

FOREIGN PATENT DOCUMENTS

| | | | | |
|---|---|---|---|---|
| DE | 2 029 766 | 12/1971 | ........... | B32B/31/00 |
| EP | 0 426 197 A2 | 5/1991 | ........... | A61F/13/46 |
| EP | 0 525 778 A3 | 2/1993 | ........... | A61F/13/15 |
| EP | 0 685 212 A2 | 12/1995 | ........... | A61F/13/15 |
| EP | 956 843 A1 | 11/1999 | | |
| FR | 2 427 795 | 1/1980 | ........... | A61B/13/02 |
| FR | 2 653 328 | 4/1991 | ........... | A61F/13/46 |
| GB | 1 211 095 | 4/1970 | ........... | A61F/13/16 |
| GB | 2 232 600 A | 12/1990 | ........... | A61F/13/15 |
| GB | 2 326 598 A | 12/1998 | | |
| JP | 5-33721 | 2/1993 | ............ | F02F/3/00 |
| JP | 5-115506 | 5/1993 | ........... | A61F/13/15 |
| JP | 5-238327 | 9/1993 | ........... | B60R/13/06 |
| WO | WO 92/07535 | 5/1992 | ........... | A61F/13/46 |
| WO | WO 94/16658 | 8/1994 | ........... | A61F/13/15 |
| WO | WO 95/16422 | 6/1995 | ........... | A61F/13/15 |
| WO | WO 98/58613 A1 | 12/1998 | | |
| WO | WO 99/55272 A1 | 11/1999 | | |

*Primary Examiner*—Weilun Lo
*Assistant Examiner*—Jacqueline F Stephens
(74) *Attorney, Agent, or Firm*—James P. Borr

(57) ABSTRACT

A compound sanitary napkin including a primary absorbent member and a secondary absorbent member, the primary absorbent member having a length and a width and the secondary absorbent member has a length and a width. The primary absorbent member includes an absorbent core and a liquid pervious topsheet superposed on the absorbent core. The secondary absorbent member includes a liquid pervious topsheet, a liquid impervious barrier sheet joined to the topsheet and an absorbent element positioned between the topsheet and the barrier sheet. The primary absorbent member has a contoured shape wherein the width of the primary absorbent member in a central region is narrower than the width at least one transverse end region.

31 Claims, 25 Drawing Sheets

U.S. PATENT DOCUMENTS

| | | | | |
|---|---|---|---|---|
| 2,662,527 A | | 12/1953 | Jacks | 128/290 |
| 2,683,457 A | | 7/1954 | Cunningham | 128/290 |
| RE24,137 E | | 4/1956 | Jacks | 128/290 |
| 2,890,700 A | * | 6/1959 | Lonberg-Holm | 128/284 |
| 2,929,379 A | | 3/1960 | Poulsen | 128/290 |
| 2,965,102 A | | 12/1960 | Harwood | 128/290 |
| 3,183,909 A | | 5/1965 | Roehr | 128/290 |
| 3,406,689 A | | 10/1968 | Hicks et al. | 128/290 |
| 3,512,530 A | | 5/1970 | Jones | |
| 3,528,422 A | | 9/1970 | Hodas | |
| 3,570,492 A | | 3/1971 | Bettencourt | |
| 3,916,900 A | * | 11/1975 | Breyer et al. | 128/287 |
| 4,046,147 A | | 9/1977 | Berg | |
| 4,195,634 A | | 4/1980 | DiSalvo et al. | |
| 4,425,130 A | | 1/1984 | DesMarais | |
| 4,576,597 A | | 3/1986 | Hlaban | |
| 4,938,756 A | | 7/1990 | Salek | |
| 5,057,096 A | | 10/1991 | Faglione | |
| 5,219,341 A | * | 6/1993 | Serbiak et al. | 604/361 |
| 5,236,428 A | | 8/1993 | Zajaczkowski | |
| 5,391,160 A | | 2/1995 | Runeman et al. | |
| 5,447,507 A | | 9/1995 | Yamamoto | |
| 5,507,735 A | | 4/1996 | Van Iten et al. | |
| 5,558,656 A | * | 9/1996 | Bergman | 604/385.1 |
| H1614 H | | 11/1996 | Mayer et al. | |
| 5,591,150 A | * | 1/1997 | Olsen et al. | 604/385.1 |
| 5,620,430 A | * | 4/1997 | Bamber | 604/385.2 |
| 5,662,633 A | * | 9/1997 | Doak et al. | 604/378 |
| 5,662,639 A | * | 9/1997 | Tanaka et al. | 604/387 |
| 5,807,362 A | * | 9/1998 | Serbiak et al. | 604/361 |
| 5,827,258 A | * | 10/1998 | McFall et al. | 604/385.1 |
| 5,853,401 A | * | 12/1998 | Mayer et al. | 604/378 |
| 5,873,869 A | * | 2/1999 | Hammons et al. | 604/385.1 |
| 5,961,508 A | | 10/1999 | Mayer et al. | |

* cited by examiner

COMPOUND NAPKIN

FIELD OF THE INVENTION

The present invention relates to disposable absorbent articles such as panty liners, sanitary napkins and adult incontinence devices that are designed and adapted to be worn in a crotch portion of a wearer's undergarment and to receive and contain menses and other vaginal discharges.

BACKGROUND OF THE INVENTION

Disposable sanitary napkins generally comprise an absorbent element interposed between a liquid pervious body-contacting layer (often referred to as a topsheet or cover layer) and a liquid impervious protective barrier layer (often referred to as a barrier sheet). The absorbent element is capable of receiving and containing liquids such as menses and other vaginal liquid discharges. The body-contacting layer is intended to provide a comfortable and dry-feeling contact with a user's body surfaces while allowing free passage of liquid therethrough into the subjacent absorbent element. The protective barrier is intended to retain the absorbed liquids within the absorbent element and thus prevent the absorbed liquids from soiling the user's garments. Disposable sanitary napkins are generally provided with an adhesive attachment means for securing the napkin to the inner crotch area of the user's undergarments. Protective side flaps may optionally be provided along the longitudinal sides of the napkin which are adapted to be folded over the edges of a crotch portion of the user's undergarment.

Disposable sanitary napkins generally come in one of three basic configurations based upon their intended use. A first product configuration is intended for the absorption of medium to high menstrual flows and is constructed with a relatively thick central absorbent element having a relatively high absorptive capacity. While having a relatively high absorptive capacity, the bulkiness of the absorbent member may cause a certain degree of wearing discomfort. A second configuration of sanitary napkins is intended for light or low menstrual flows. These sanitary napkins have a thin flexible structure and are commonly referred to as panty-liners or panty-shields. A third type of sanitary napkin is intended for absorption of medium to high menstrual flows and has a thin, flexible structure and has a relatively high absorptive capacity. The relatively high absorptive capacity is achieved by providing the thin absorbent element with superabsorbent particles. These sanitary napkins are commonly referred to as ultra-thin sanitary napkins.

Another class of sanitary napkins has recently been developed that combines one or more of these concepts into a single compound sanitary napkin. A compound sanitary napkin has a primary menstrual pad and an undergarment protector that are joined to one another to form a unitary structure. Compound sanitary napkins of this design have been disclosed in U.S. Pat. No. 4,425,130 to DesMarais and Statutory Invention Registration H1614 to Mayer et al. In accordance with these references, the primary menstrual pad is intended to absorb the bulk of the bodily liquids discharged by the user, while the undergarment protector is intended to protect the user's garments from soiling. In use, the relative freedom of movement between the primary menstrual pad and the undergarment protector serves to maintain the primary menstrual pad adjacent the user's crotch region while the undergarment protector remains associated with the user's undergarment.

The primary menstrual pad is disclosed as being narrow enough to at least reside partially within the external genitalia. Optionally, the primary menstrual pad may be wider than the width of the labia majora, but the primary menstrual pad should exhibit a lateral compression or conformability at relatively low forces, such as the forces exerted by the soft tissue of the female external genitalia, such that a portion of the primary menstrual pad is able to at least reside partially within the external female genitalia. By being conformable at relatively low forces, the primary absorbent member remains comfortable during use. In addition, the primary menstrual pad preferably exhibits a resilient recovery to enable the pad to conform to the body as the pad and body interface is subjected to shape changes. As the primary menstrual pad is made narrower to fit the body, the undergarment protector preferably remains sufficiently wide enough to provide a stable attachment to the wearer's undergarment and to sufficiently cover the undergarment to protect it from soiling.

SUMMARY OF THE INVENTION

In accordance with the present invention there has been provided a novel compound sanitary napkin comprising a primary absorbent member and a secondary absorbent member. The primary absorbent member has a contoured shape wherein the width of the primary absorbent member varies along its length such that the width in a central region is less than the width of the primary absorbent member in at least one of the transverse end regions. The primary absorbent member includes an absorbent core and a liquid pervious topsheet superimposed on a body facing side of the absorbent core and a separate layer of flexible material forming a backsheet superimposed on a garment facing side of the absorbent core, the topsheet and backsheet covering opposite major surfaces of the absorbent core. The backsheet may optionally be formed from a flexible liquid impervious polymeric film to act as a liquid barrier on the garment facing side of the absorbent core. The secondary absorbent member includes a liquid pervious topsheet, a liquid impervious barrier sheet joined to the topsheet and an absorbent element positioned between the topsheet and the barrier sheet. The primary absorbent member is affixed to at least a portion of the secondary absorbent member by union means in the transverse end regions and may optionally be affixed to the secondary absorbent member along a substantial portion of the length of the primary absorbent member. The secondary absorbent member preferably comprises an adhesive attachment means for securing the compound sanitary napkin to the crotch portion of the user's undergarment. In addition, the secondary absorbent member preferably comprises flexible, protective side flaps along the longitudinal sides of the absorbent member which are adapted to be folded over the edges of a crotch portion of the user's undergarment. The uppermost primary absorbent member has a length, a width, opposite transverse ends and a center region intermediate the transverse ends. The lowermost secondary absorbent member is located under the primary absorbent member, and also has a length, a width, and opposite transverse ends.

Also provided in accordance with the present invention is a novel compound sanitary napkin adapted to be placed in a crotch portion of an undergarment and to be worn in a groin region of a female user. The compound sanitary napkin comprises an uppermost primary absorbent member and a lowermost secondary absorbent member. The primary absorbent member includes a body-facing liquid pervious topsheet, a garment facing backsheet and an absorbent core between the topsheet and the backsheet, the primary absorbent member having a first transverse end and an opposite second transverse end defining therebetween a length. The primary absorbent member also has a first longitudinal side edge and an opposite second longitudinal side edge defining therebetween a width. Located between the first and second transverse ends is a center region. The first transverse end, the second transverse end and the center region each having a respective width, wherein the width of the center region is less than the width of the first transverse end. The secondary absorbent member includes a body-facing liquid pervious topsheet, a garment-facing liquid impervious barrier sheet and an absorbent core between the topsheet and the barrier sheet. The barrier sheet is joined to the topsheet around respective peripheral edge portions of the topsheet and barrier sheet to form a liquid impervious flange seal that defines the outer side edges of the secondary absorbent member. The primary absorbent member is affixed to at least a portion of the liquid pervious topsheet of the secondary absorbent member and the width of the primary absorbent member in a center region thereof is adapted to span the groin region of the user and to contact and gently compress the user's labia majora.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

Figure 1:
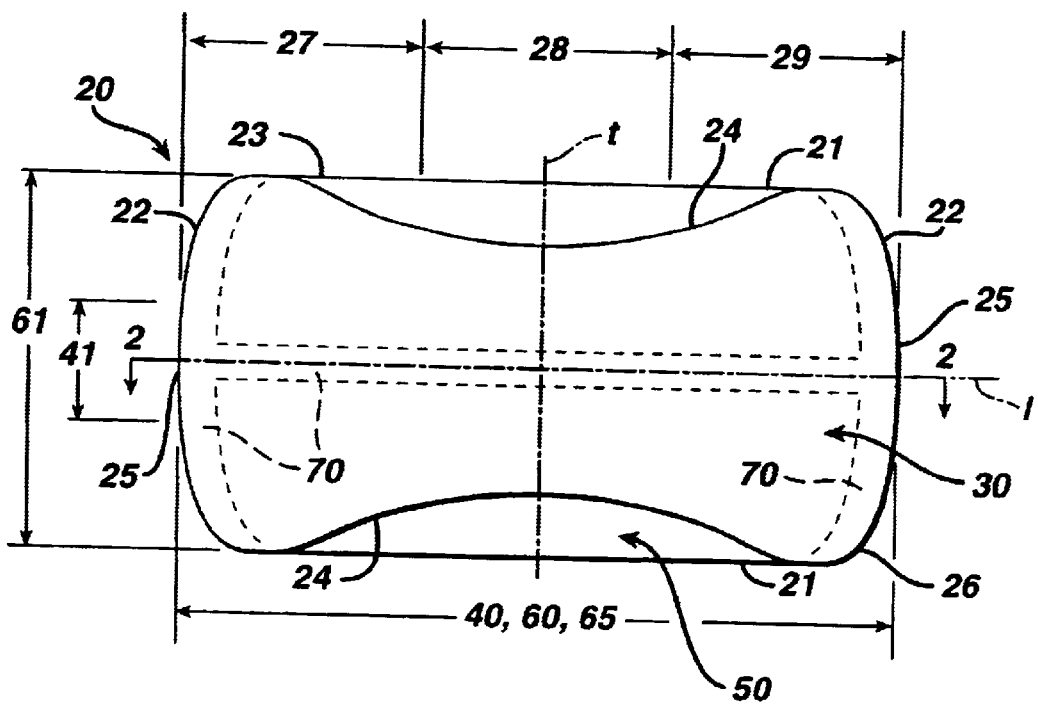
FIG. 1 is a top plan view of one embodiment of the compound sanitary napkin of the present invention.

The present invention is directed to a compound sanitary napkin that is adapted to provide enhanced body fit, to absorb body liquids and to protect a user's garments from being soiled. The term "sanitary napkin", as used herein, refers to a disposable article which is worn by females in a crotch portion of an undergarment adjacent to the pudendal region and which is intended to absorb and retain the various liquid exudates which are discharged from the body (e.g., blood, menses, and urine). The term "compound sanitary napkin", as used herein, refers to a sanitary napkin comprised of separate constituents joined to one another to form a unitary structure. Inter-labial devices that reside partially within and partially external of the wearer's vestibule are also within the scope of this invention. As used herein, the term "pudendal" refers to the externally visible female genitalia and includes the labia majora, the labia minora, the clitoris, and the vestibule.

Referring now to FIGS. 1–3D, there is shown one embodiment of a compound sanitary napkin 20 of the present invention. As can be seen, the compound sanitary napkin 20 comprises a primary absorbent member 30 and a secondary absorbent member 50 joined together by union means 70. The compound sanitary napkin has two surfaces, an upper body contacting or body facing surface, and a lower, garment facing or garment contacting surface. The primary and secondary absorbent members each have corresponding body facing and garment facing surfaces. The compound sanitary napkin 20 has two centerlines, a longitudinal centerline and a transverse centerline. The term "longitudinal", as used herein, refers to a line, axis or direction within the plane of the compound sanitary napkin that is generally parallel to a vertical plane which bisects a standing wearer into left and right body halves when the compound sanitary napkin is worn. The term "lateral", as used herein refers to a line, axis, or direction which lies within the plane of the compound sanitary napkin that is generally perpendicular to the longitudinal direction.

The primary absorbent member 30 has opposite longitudinally extending sides 24 defining therebetween a width and opposite laterally extending transverse ends 25 defining therebetween a length. Thus as used herein, the terminology "width" refers to a measurement taken in a lateral direction, substantially perpendicular to the longitudinal centerline, between the opposite longitudinally extending sides of the respective absorbent member and the terminology "length" refers to a measurement taken in a longitudinal direction, substantially parallel to the longitudinal centerline, between the opposite transverse ends of the respective absorbent member. The sides 24 and the transverse ends 25 together define the periphery 26 of the primary absorbent member. The secondary absorbent member 50 has opposite longitudinally extending sides 21 defining therebetween a width and opposite laterally extending transverse ends 22 defining therebetween a length and which together define the periphery 23 of the secondary absorbent member. The length defined between the transverse ends 25 of the primary absorbent member may the same as the length defined between transverse ends 22 of the secondary absorbent member, or alternatively, the transverse ends 25 of the primary absorbent member may be slightly inset from the transverse ends 22 of the secondary absorbent member and thus the length of the primary absorbent member may be less than the length of the secondary absorbent member. Similarly, the width defined between the sides 24 of the primary absorbent member 30 may be the same as at least a portion of the width defined between the sides 21 of the secondary absorbent member or, alternatively, the primary absorbent member 30 may have a width that is less that the width of the secondary absorbent member in all regions of the compound sanitary napkin. In any of these embodiments, since the sides 24 and transverse ends 25 of the primary absorbent member are always less than or equal to the sides 21 and transverse ends 22 of the secondary absorbent member, the periphery 23 of the secondary absorbent member will define the periphery of the compound sanitary napkin 20.

Figure 4:
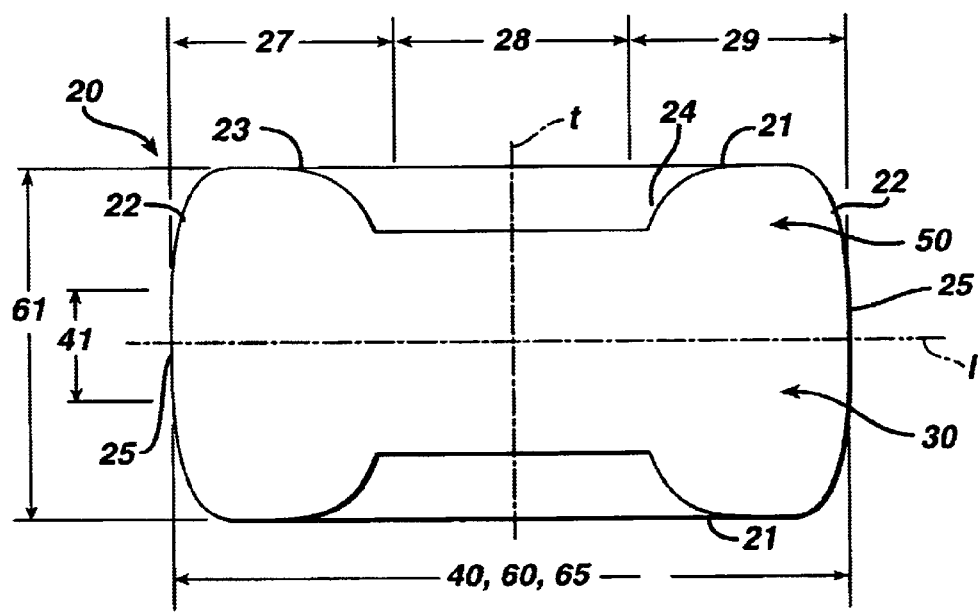
FIG. 4 is a top plan view of another embodiment of a compound sanitary napkin of the present invention.
Figure 5:
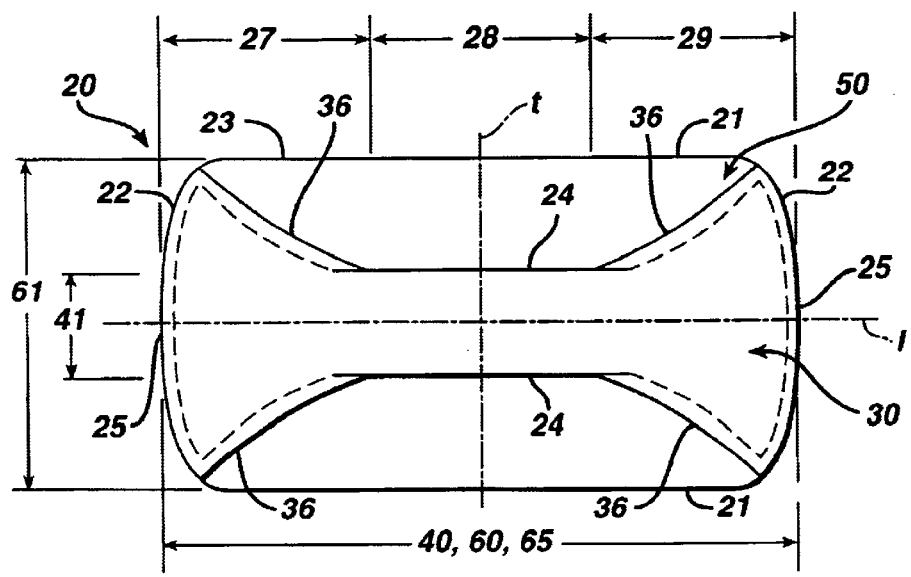
FIG. 5 is a top plan view of another embodiment of a compound sanitary napkin of the present invention.

The primary absorbent member 30 has a contoured shape wherein the width of the primary absorbent member varies along its length such that the width in a central region is less than the width of the primary absorbent member in at least one of the transverse end regions. In the embodiment shown in FIG. 1, the primary absorbent member has a substantially hourglass shape wherein both transverse end regions are wider than the central region and wherein the longitudinal sides have a curved or arcuate shape. Alternatively, as shown in FIGS. 4 and 5, the contoured hourglass shape may have a more angular shape such as a dog-bone shape wherein the narrower center region has substantially parallel straight sides. It has been found that primary absorbent members having the above-described contoured shapes will closely approximate the anatomical shape of the crotch region of the user and substantially enhances the comfort of the compound sanitary napkin to the user. In addition, the contoured shape of the primary absorbent member enhances the effectiveness of the compound sanitary napkin to absorb liquids and prevent leaks by enabling the primary absorbent member 30 to maintain better body contact with the user and thus acquire body exudate at the instant that it exits the body.

FIG. 5 illustrates another embodiment of the invention. In accordance with this embodiment, compound napkin of the invention has a primary absorbent member 30 having a flange seal 36 that extends only in the transverse end regions of the primary absorbent member 30, the centrally located side edges 24 being formed by wrapping the cover layer under the absorbent core and then sealing or affixing the cover layer to the secondary absorbent member 50.

The primary absorbent member 30 is sized and configured to contact the body of the user and is intended to absorb the bulk of bodily liquids discharged by the user. The primary absorbent member 30 comprises an absorbent means 33, such as absorbent core 34, a liquid permeable topsheet 32 superimposed on the absorbent core 34 and a backsheet 35. The primary absorbent member 30 has opposite longitudinally extending sides 24 in a contoured shape having first and second opposite transverse end regions with at least one end region having a relatively greater width and a center region having a relatively smaller or narrower width. As used herein, center region or central region of the primary absorbent member refers to a region of the primary absorbent member intermediate the transverse ends that is adapted to contact a wearer's pudendum when the compound sanitary napkin is worn in a crotch portion of the wearer's undergarment. It should be noted that the central region of the primary absorbent member may be located nearer to one transverse end of the primary absorbent member and need not be located in the exact midpoint of the absorbent member where the longitudinal centerline intersects with the transverse centerline and bisect the absorbent member into two equal halves. Thus, while some embodiments of the present invention may include a compound sanitary napkin that is substantially symmetrical such that the center region is located substantially in the exact midpoint of the both the primary and secondary absorbent members, other embodiments of the present invention may include compound sanitary napkins that are asymmetrical wherein the center region does not coincide with the intersection of the longitudinal centerline axis and the lateral centerline axis. One example of an asymmetrical sanitary napkin is an overnight type of sanitary napkin having a relatively narrow central region that is adapted to be worn in a crotch portion of an undergarment and having a relatively wider transverse end region that has an extended length that is sufficiently long to cover at least a portion of a users gluteal crease when the central region is placed in the crotch region of the undergarment.

Figure 6:
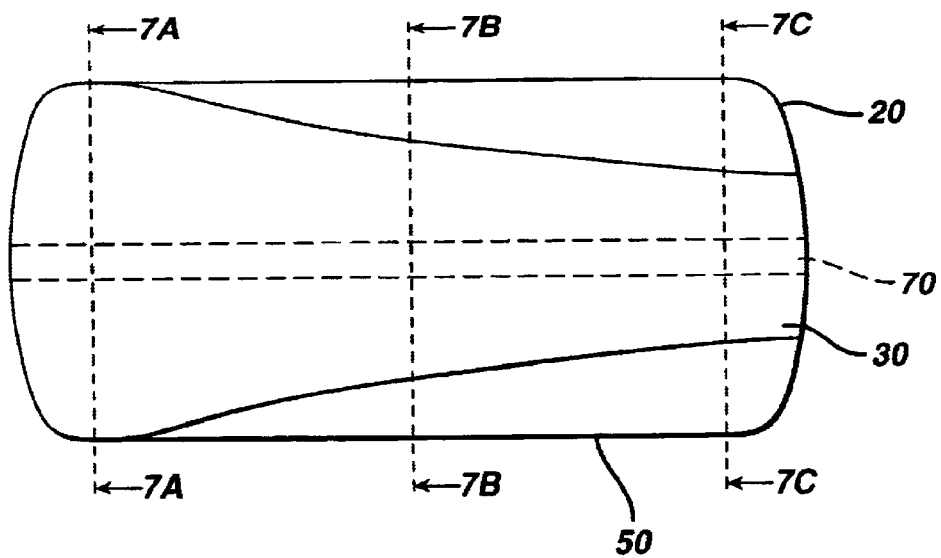
FIG. 6 is a top plan view of another embodiment of a compound sanitary napkin of the present invention.
Figure 7A:
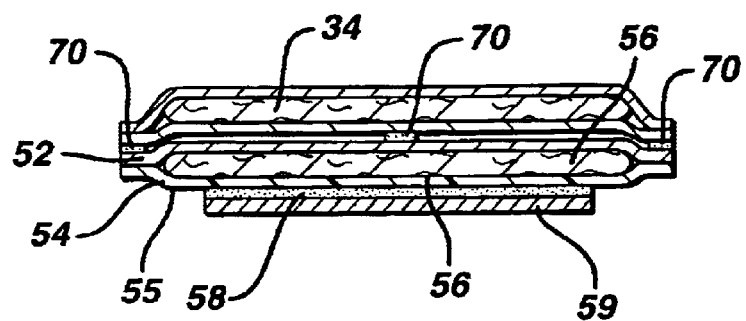
FIG. 7A is a cross-sectional view of the compound sanitary napkin shown in FIG. 6 as taken along section line 7A—7A.
Figure 7B:
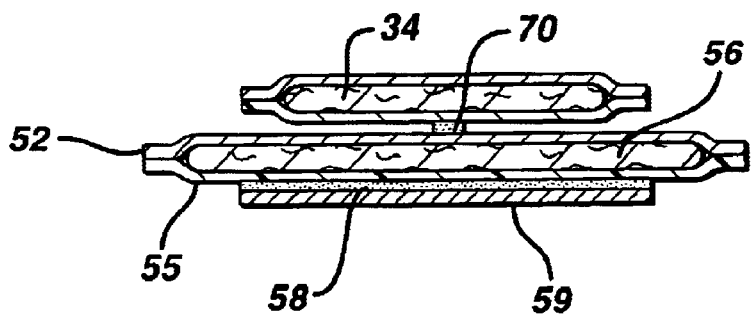
FIG. 7B is a cross-sectional view of the compound sanitary napkin shown in FIG. 6 as taken along section line 7—7B.
Figure 7C:
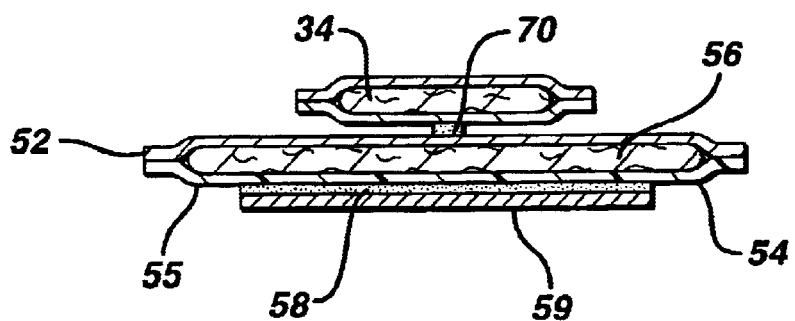
FIG. 7C is a cross-sectional view of the compound sanitary napkin shown in FIG. 6 as taken along section line 7C—7C.
Figure 8:
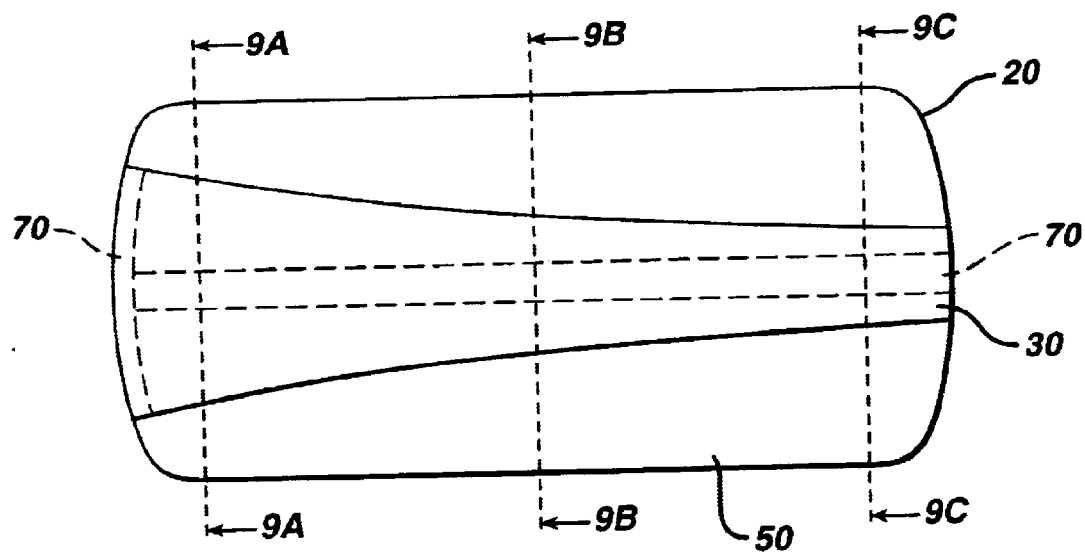
FIG. 8 is a top plan view of another embodiment of a compound sanitary napkin of the present invention.
Figure 9A:
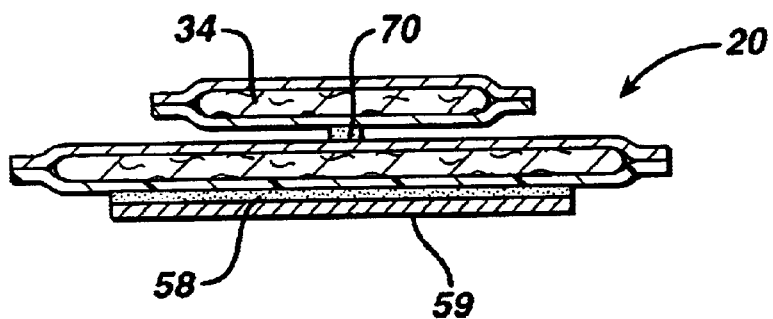
FIG. 9A is a cross-sectional view of the compound sanitary napkin shown in FIG. 8 as taken along section line 9A—9A.
Figure 9B:
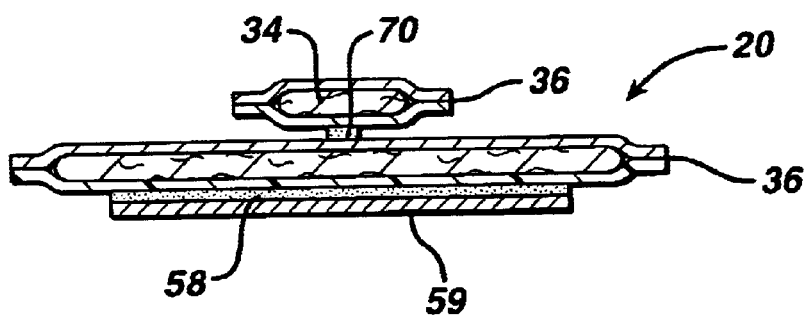
FIG. 9B is a cross-sectional view of the compound sanitary napkin shown in FIG. 8 as taken along section line 9B—9B.
Figure 9C:
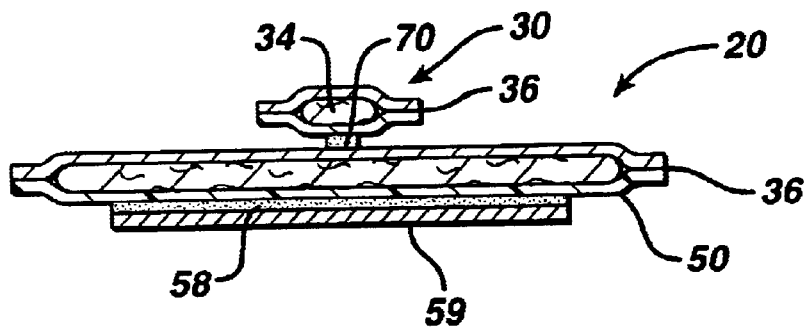
FIG. 9C is a cross-sectional view of the compound sanitary napkin shown in FIG. 8 as taken along section line 9C—9C.
Figure 10:
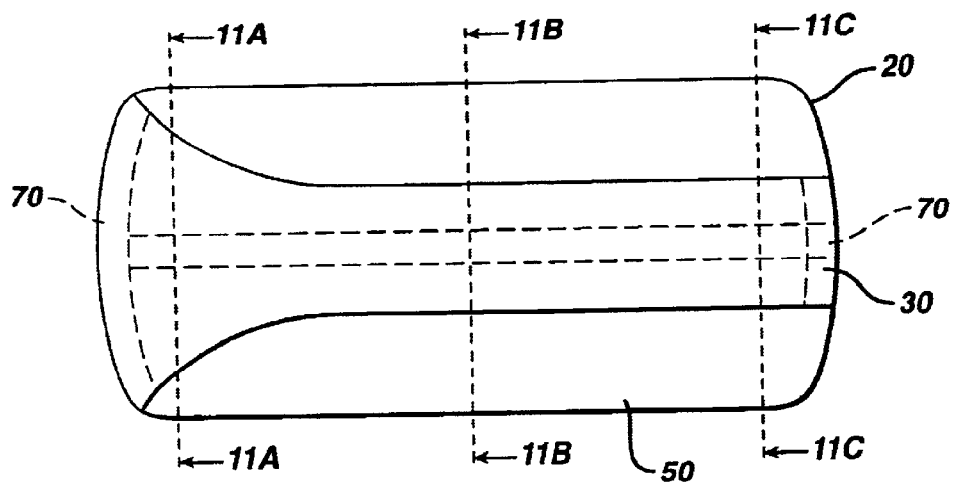
FIG. 10 is a top plan view of another embodiment of a compound sanitary napkin of the present invention.
Figure 11A:
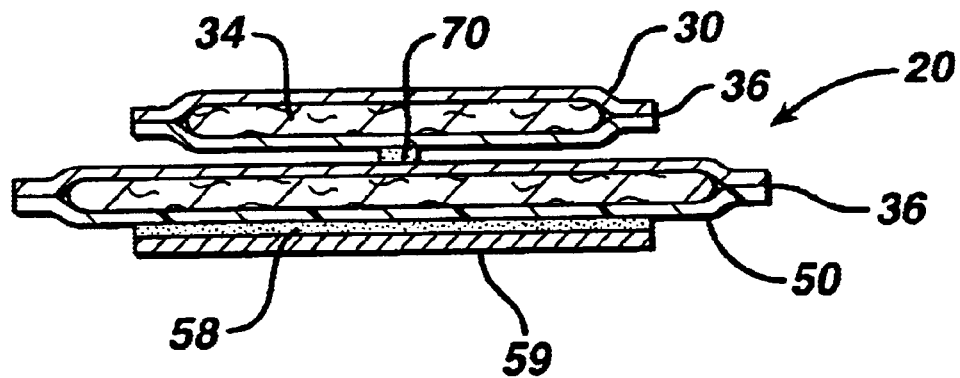
FIG. 11A is a cross-sectional view of the compound sanitary napkin shown in FIG. 10 as taken along section line 11A—11A.
Figure 11B:
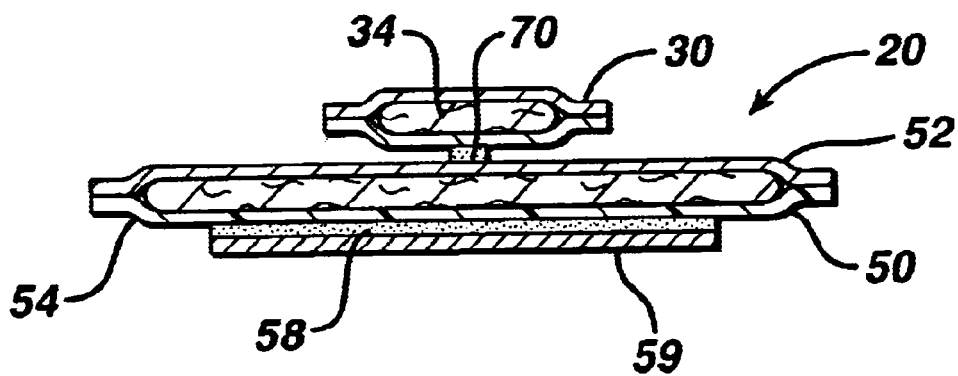
FIG. 11B is a cross-sectional view of the compound sanitary napkin shown in FIG. 10 as taken along section line 11B—11B.

Referring to FIGS. 6–11C, there is shown another embodiment of the present invention wherein the primary absorbent member has a contoured shape which is in the form of a taper. In accordance with this embodiment a first transverse end region has a relatively wider width than any other portion of the primary absorbent member including the center region and the opposite second transverse end region. In one embodiment, as shown in FIGS. 6–7C the width of the primary absorbent member is substantially the same as the width of the secondary absorbent member in a first transverse end region. In addition, the width of the primary absorbent member substantially continuously decreases from the first transverse end region to the opposite transverse end region. In another embodiment, as shown in FIGS. 8–9C the width of the primary absorbent member is less than the width of the secondary absorbent member in a first transverse end region. However, this embodiment is similar to that shown in FIGS. 6–7C in that the width of the primary absorbent member substantially continuously decreases from the first transverse end region to the opposite transverse end region. In yet another alternative embodiment, as shown if FIGS. 10–11B, the contoured tapered shape may have substantially straight, parallel side portions wherein a first transverse end region tapers toward a narrower center region and opposite transverse end region, these regions having substantially parallel, straight longitudinal sides. It has been found that primary absorbent members having the above-described contoured shapes will closely approximate the anatomical shape of the crotch region as well as the gluteal crease of the user and substantially enhances the comfort and stability of the compound sanitary napkin in use. In a preferred embodiment of the present invention, the primary absorbent member has a tapered end region adapted to comfortably fit in a user's gluteal crease. The contoured, tapered shape of the primary absorbent member has also been found to enhance the effectiveness of the compound sanitary napkin to absorb liquids and prevent leaks by enabling the primary absorbent member 30 to maintain better body contact with the user and thus acquire body exudate at the instant that it exits the body. In accordance with this embodiment of the invention, the primary absorbent member is sized and configured to at least span the user's labia majora and preferably spans the user's groin region with minimal bunching which may be imparted by the laterally compressive forces of the user's thighs. Optionally, a portion of the primary absorbent member may reside within the user's labial groove. It is preferred that the width of the primary absorbent member 30 in the center region be from about 10 mm to 65 mm. The width of the primary absorbent member at its wider transverse end region (s) may be from about 20 mm to 95 mm and is preferably from about 30 mm to about 75 mm.

The primary absorbent member of the present invention is preferably relatively conformable. It is preferred to keep the primary absorbent member relatively conformable so that when worn by a user, at least a portion of the primary absorbent member may conform to the contours of the pudendal region. By forming the primary absorbent member from conformable materials, it is possible that a portion of the primary absorbent member may comfortably fit or reside within at least a portion of the labial groove. While primary absorbent members have been described above as having widths or diameter dimensions greater than the width of the labial groove, they too may fit within the labial groove if they are sufficiently conformable.

The width of the primary absorbent member 30 in the center region can vary widely depending on the thickness of the compound sanitary napkin. More particularly, if the combined thickness' of the primary absorbent member 30 and the secondary absorbent member 50 result in a relatively thick, bulky sanitary napkin, i.e. having a caliper greater than 5 mm, then the width of the absorbent structure 33 within the primary absorbent member 30 in the center region should be relatively narrow, generally from about 10 mm to 40 mm. Conversely, if the combined thickness' of the primary absorbent member 30 and the secondary absorbent member 50 result in a relatively thin (between 3 mm and 5 mm) or ultra-thin (less than 3 mm) sanitary napkin, then the width of the absorbent structure 33 within the primary absorbent member 30 in the center region may be relatively wider and still provide a comfortable, non-irritating sanitary napkin. In a preferred embodiment, the combination of the primary absorbent member 30 and the secondary absorbent member 50 have a thickness of less than 5 mm, and the width of the primary absorbent member in the center region is from about 10 mm to about 65 mm, preferably from about 20 mm to about 40 mm.

The length 40 of the primary absorbent member 30 can be of any convenient dimension and will generally range from about 2 to 35 cm long, preferably from about 10 to 35 cm long, and more preferably from about 20 to 35 cm long. A particularly preferred primary absorbent member 30 has a length of about 24 cm.

The topsheet 32 is preferably compliant, soft feeling, and non-irritating to the wearer's skin. Further, the topsheet 32 is liquid pervious, permitting liquid to readily penetrate through its thickness. A suitable topsheet 32 may be manufactured from a wide range of materials such as woven fabrics, nonwoven fabrics, polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven fabrics can be comprised of natural fibers (e.g., wood or cotton fibers), synthetic fibers (e.g., polymeric fibers such as polyester, polypropylene, or polyethylene fibers); or from a combination of natural and synthetic fibers. A preferred topsheet is a non-woven fabric formed from a blend of three denier and five denier polypropylene fibers. These non-woven fabrics are commercially available from Stearns Technical Textiles Co. having an address at 100 William Street, Cincinnati, Ohio 45215, or PGI Nonwovens, Chicopee Inc., having an address at 2351 US Route 130 Dayton, N.J. 08810-1004.

Alternatively, the topsheet may comprise an apertured, formed film. Preferably the apertured formed film is a three dimensional apertured formed film that is pervious to body exudates, non-absorbent and having a reduced tendency to allow liquids to pass back through and rewet the wearer's skin. Thus, the surface of the formed film that is in contact with the body remains dry, thereby reducing body soiling and creating a more comfortable feel for the wearer. In a preferred embodiment of the present invention, the body-facing or exposed surface of the formed film topsheet is hydrophilic to help liquid transfer through the topsheet faster than if the body-facing surface was not hydrophilic. A rapid transfer of liquid through the topsheet has been found to diminish the likelihood that menstrual liquid will flow off the topsheet and to increase the likelihood that menstrual liquid will flow into and be absorbed by the absorbent core. In a preferred embodiment, surfactant is incorporated into the polymeric materials of the formed film topsheet. Alternatively, the body surface of the topsheet can be made hydrophilic by treating it with a surfactant.

To insure proper liquid transfer between the topsheet 32 and the subjacent absorbent structure 33, it is preferred that the topsheet be substantially continuously secured to the underlying absorbent structure 33 throughout their common association or interface. As shown if FIG. 3A, the absorbent structure 33 comprises only absorbent core 34. By substantially continuously securing the topsheet 32 to the underlying absorbent core 34, the topsheet 32 will have a reduced tendency to separate from the absorbent core 34 during use. Separation of the absorbent core from the topsheet 32 may inhibit liquid transfer from the top sheet 32 into the underlying absorbent core 34. The topsheet 32 may be secured to the absorbent core 34 in any suitable manner including, but not limited to spray gluing or applying lines or spots of adhesives between the topsheet 32 and the absorbent core 34. Alternatively, or additionally, the topsheet 32 may be secured to the absorbent core 34 by entangling the fibers of the absorbent core 34 with the topsheet 32, by fusing the topsheet 32 to the absorbent core 34 with a plurality of discrete individual fusion bonds. In the embodiment illustrated in FIG. 3C, absorbent structure 33 comprises not only absorbent core 34, but also liquid acquisition layer 46. In accordance with this embodiment, the topsheet 32 is secured to liquid acquisition layer 46 rather than absorbent core 34.

The topsheet 32 of the primary absorbent member 30 may be formed of one material while the topsheet 52 of the secondary absorbent member 50 may be of another material. In a preferred embodiment, topsheet 32 of the primary absorbent member 30 is formed from an apertured polymeric film and topsheet 52 of secondary absorbent member 50 is formed from a nonwoven fabric.

Referring again to FIGS. 2–3D, it can be seen that the separate layers forming the topsheet 32 and backsheet 35 are joined together at a peripheral edge to form a flange 36 to completely encase or enclose the absorbent core 34 of the primary absorbent member 30. The flange seal 36 comprises a laminate of topsheet 32 and backsheet 35 and generally has a width dimension of from about 1 mm to about 10 mm and is preferably about 5 mm. The use of separate layers for the topsheet and backsheet is advantageous because it permits greater flexibility in napkin design and ease in high speed manufacturing processes. While the presence of a flange seal along the longitudinal sides of the primary absorbent member was expected to cause irritation to the user due to the proximity of the flange to sensitive tissue area of the user, it has been found not to cause any irritation or discomfort to the user. In a preferred embodiment, the topsheet 32 is draped over the absorbent core 34 such that it covers at least a portion of the longitudinal side edges of the absorbent core 34 and is then sealed to the backsheet 35 along flange seal 36. When viewed in cross section, the flange seal 36 is located between the plane defined by the topsheet 32 and the plane defined by the backsheet 35 of the primary absorbent member 30. Alternatively, the topsheet 32 drapes around the absorbent core 34 and is sealed to the backsheet 35 substantially within the same plane as the plane defined by the backsheet 35, creating what is commonly termed a positive profile.

The absorbent core 34 may be formed from any absorbent materials which are generally soft, compliant, comfortable and non-irritating to the wearer's skin and capable of absorbing and containing body exudates. Preferably, the absorbent core is compressible such that the primary absorbent member will deform under relatively small forces that are experienced during normal use. In addition to being compressible, the materials comprising the absorbent core are preferably conformable such that the primary absorbent member is able to provide improved fit into and/or around the labia and perineum. While being generally compressible and conformable under relatively small forces, those forces exerted by the external female genitalia during use, it is also important that the primary absorbent member be sufficiently resilient such that when subjected to normal wearing forces it does not permanently collapse. Preferably, the primary absorbent member will be sufficiently resilient that it will conform to the contours of the body to provide intimate contact with the exposed genitalia of the female user. Intimate contact with the exposed female genitalia helps provide better liquid transfer from the user into the primary absorbent member without allowing liquid to bypass and/or run-off the primary absorbent member. While the resilient characteristics of the absorbent core 34 allow for improved fit, they must be balanced against the need for the product to be both soft and comfortable for the wearer. The absorbent core 34 may be manufactured from a wide variety of liquid absorbent materials commonly used in disposable sanitary napkins, and other disposable absorbent articles. Examples of suitable absorbent materials include, but are not limited to comminuted wood pulp (which is generally referred to as pulp fluff), creped cellulose wadding, modified cross-linked cellulose fibers, capillary channel fibers (that is, fibers having intra-fiber capillary channels which are well known in the art), absorbent foams, thermally bonded airlaid materials, absorbent sponges, synthetic staple fibers, polymeric fibers, hydrogel-forming polymer gelling agents, peat moss, or any equivalent materials or combinations thereof.

The total absorbent capacity of the absorbent core 34 should be compatible with the intended exudate loading for the compound sanitary napkin 20. Further, the absorbent capacity of the absorbent core 34 may be varied to accommodate wearers ranging in the expected amount of exudate liquid volume. For instance, a different absorbent capacity may be utilized for compound sanitary napkins intended for daytime use as compared with those intended for night time use, or for compound sanitary napkins intended for use by teenage females as compared with those intended by more mature women.

Figure 3A:
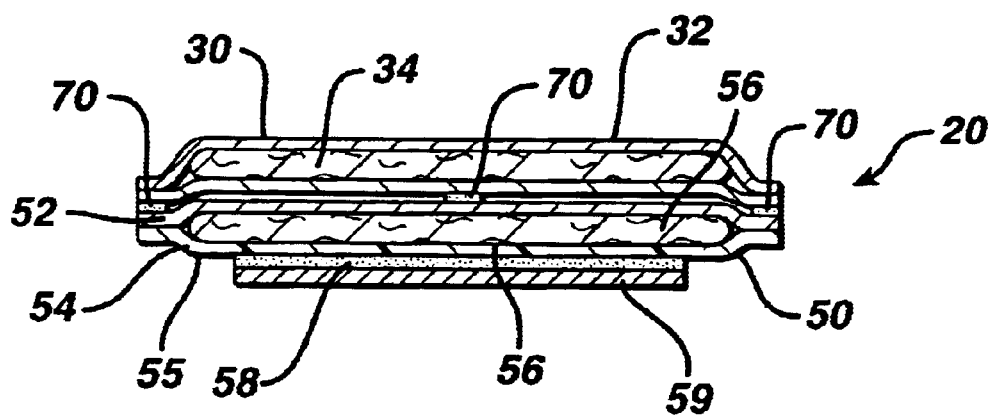
FIG. 3A is a cross-sectional view of the compound sanitary napkin shown in FIGS. 1 and 2 as taken along section line 3A—3A of FIG. 2.
Figure 3B:
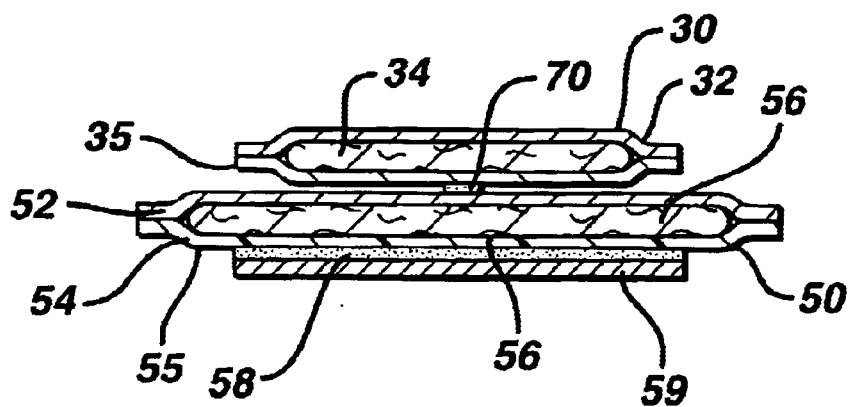
FIG. 3B is a cross-sectional view of the compound sanitary napkin shown in FIGS. 1 and 2 as taken along section line 3B—3B of FIG. 2.
Figure 3C:
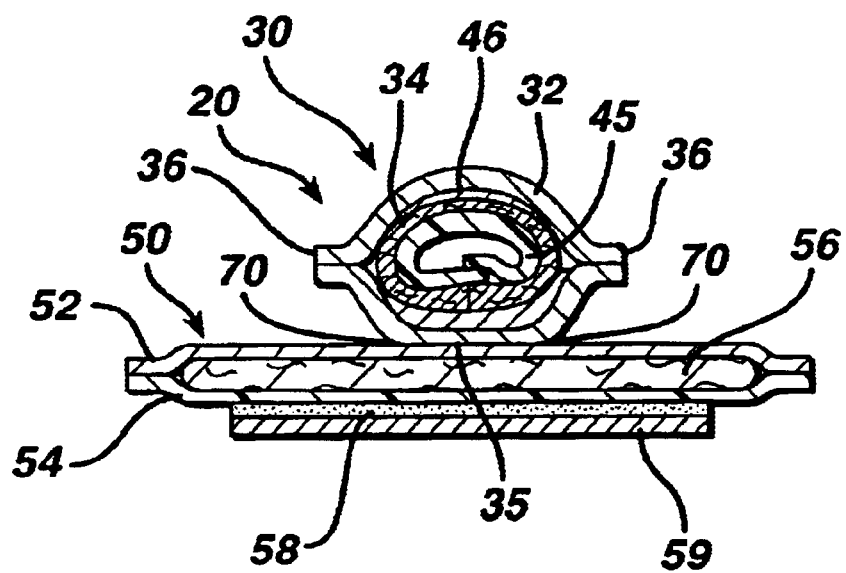
FIG. 3C is a cross-sectional view of another embodiment of a compound sanitary napkin of the present invention.
Figure 3D:
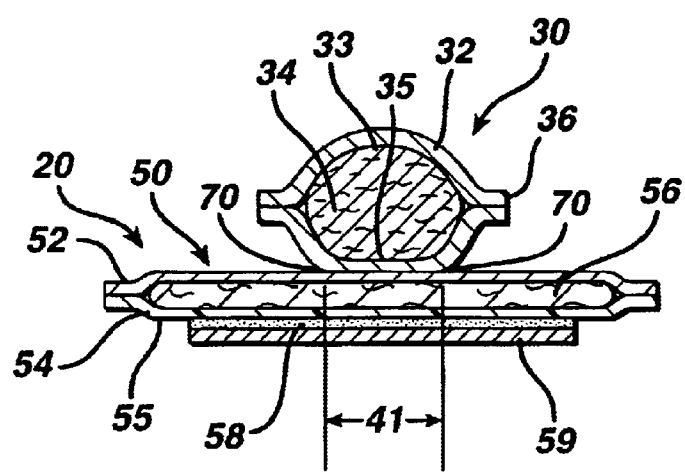
FIG. 3D is a cross-sectional view of another embodiment of a compound sanitary napkin of the present invention.

In the embodiment illustrated in FIGS. 3A and 3B, the absorbent core 34 is comprised of defiberized pulp fluff. The pulp fluff absorbent core may be manufactured in a substantially rectangular or cylindrical shape having substantially parallel straight longitudinal side edges, or alternatively may have a generally tapered shape to provide the primary absorbent member 30 with a generally tapered central region and at least one generally wider end region or optionally two wider end regions. As illustrated in FIG. 3C, the absorbent core may optionally be formed from absorbent foam or a combination of pulp fluff and foam. In this embodiment, the foam is folded or rolled such that it exhibits a generally circular cross-section. While the central region of the core 34 as shown in FIG. 3A is substantially planar, it may optionally have a generally circular or slightly oval cross-section as shown in FIGS. 3C and 3D. However, it is preferred that if the central region has a circular cross-section, the transverse end regions of the core, as shown in FIG. 3B, has a generally planar, oval or oblong cross-section to provide a tapered profile to the primary absorbent member. The absorbent core may be manufactured in a wide variety of shapes such as rectangular, triangular, oval, square, pentagonal, U-shaped, Z-folded, etc.

Optionally, the absorbent foam is preferably resilient and as illustrated in FIG. 3C forms a resilient member 45 in the primary absorbent member 30. The resilient member 45 may comprise a single member or a plurality of individual members. Alternative materials which may be used to form the resilient member 45 include, but are not limited to, nylon, polypropylene, polyurethane, polyethylene, polyester, synthetic rubber, and other synthetic materials such as formed films, or natural materials such as rubber, sponges, and the like or any suitable material which is capable of resisting collapse and permanent deformation under normal wearing conditions of sanitary napkins during use. The resilient member 45 may be manufactured in a wide variety of shapes such as rectangular, triangular, oval, square, pentagonal, U-shaped, Z-folded, etc. While the primary absorbent member can be generally of any cross-sectional shape in its unstressed condition it is preferably circular or oval in cross-section.

The resilient member 45 may extend throughout the entire length of the primary absorbent member 30 or alternatively. The resilient member 45 may only extend through a portion of the length of the primary absorbent member 30. The resilient member 45 may be positioned within the first end region 27, the central region 28, the second end region 29 or any combination of the above. For example, the resilient member 45 may be positioned in either the first end region 27 or the second end region 29 of the primary absorbent member, in both the first end region 27 and the second end region 29 of the primary absorbent member, in the central region 28 of the primary absorbent member, or in the central region 28 and the end regions 27, 29 of the primary absorbent member. In a preferred embodiment, the resilient member 45 is located in the central region 28.

Referring again to FIG. 3C, the resilient member 45 and the primary absorbent member 30 is shown as having a generally circular or oval cross-sectional configuration. Preferably, the primary absorbent member exhibits a "stationary resistance" sufficient enough to provide enhanced performance. As used herein, the term "stationary resistance" refers to the resistance exhibited by the primary absorbent member to forces applied to the primary absorbent member within the central region such that the side edges of the primary absorbent member do not extend beyond the side edges of the secondary absorbent member. In other words, the stationary resistance describes the relative movement of the primary absorbent member compared to the secondary absorbent member. It is preferred, that the longitudinally extending side edges of the primary absorbent member in its central region do not extend beyond the longitudinally extending side edges of the secondary absorbent member in its central region even under relatively high forces. By keeping the side edges of the primary absorbent member in the central region within the side edges of the central region of the secondary absorbent member, under relatively high forces, the opportunity for liquid to bypass or be expelled from the primary absorbent member and onto a surface other than the secondary absorbent member, for example, the user's skin or undergarments, is substantially reduced.

One suitable apparatus for the determination of the stationary resistance includes a scale and a resistance member. A suitable scale is a Sartorius Universal Balance. The resistance member is a cylindrical rod having a diameter of 1 inch (2.54 cm). The resistance member preferably has a length of about 6 inches (15.24 cm) The resistance member may be made of any suitable material capable of withstanding the forces during the stationary resistance procedure. Suitable materials include but are not limited to, steel, aluminum, plastic, and wood, etc.

The procedure for the stationary resistance test described more fully in Statutory Invention Registration H1614 to Mayer et al. which is incorporated herein in its entirety. As disclosed more fully therein, a resistance member is placed on a scale. The scale is then tared to zero the scale. A compound sanitary napkin having a primary absorbent member and a secondary absorbent member is placed on the testing apparatus such that the primary absorbent member resides on resistance member. The barrier sheet portion of the secondary absorbent member should be aligned substantially parallel to the axis of the resistance member. A force is applied to each end of the secondary absorbent member. Force should be applied until the side edge of the primary absorbent member is equal with the side edge of the secondary absorbent member as viewed substantially perpendicular to the topsheet portion of the secondary absorbent member. Once the side edges of the respective primary absorbent member and secondary absorbent member are aligned, a force reading the nearest gram is recorded. This reading indicates the stationary resistance of the primary absorbent member.

The primary absorbent member may exhibit a stationary resistance greater than about 600 grams. Preferably, the primary absorbent member exhibits a stationary resistance greater than or equal to 50 grams, more preferably greater than or equal to 100 grams, and most preferably greater than or equal to 150 grams.

Referring again to FIGS. 3A–3D, the primary absorbent member 30 comprises a backsheet 35. The backsheet 35 may optionally be liquid impervious to provide a liquid barrier that tends to contain absorbed liquids within the absorbent core 34. In accordance with this embodiment, the backsheet 35 may be constructed from materials having the same properties as the liquid impervious barrier sheet on the secondary absorbent member 50 described hereinafter. Alternatively, the backsheet 35 may be formed from liquid pervious material to permit absorbed liquids to flow through the backsheet 35 and thus be absorbed and retained by the subjacent secondary absorbent member. In accordance with this embodiment of the invention, the backsheet 35 may be constructed from materials having the same properties as the topsheet 35, as previously described.

Figure 2:
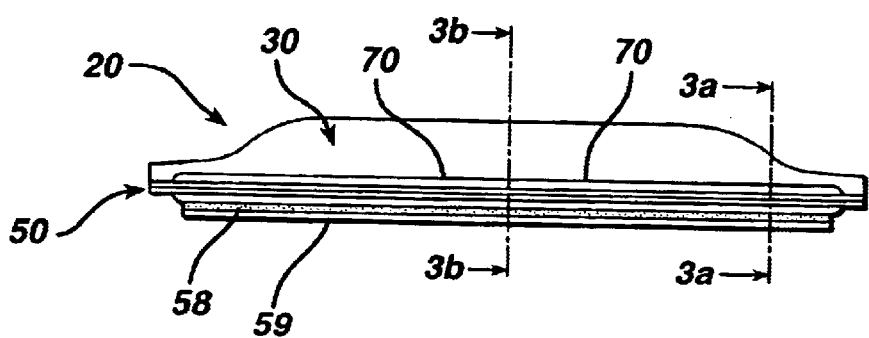
FIG. 2 is a side elevation view of the compound sanitary napkin shown in FIG. 1 as taken along section lines 2—2 of FIG. 1.

Referring to FIGS. 2–3D, the backsheet 35 of the primary absorbent member 30 is affixed to the topsheet 52 of the secondary absorbent member 50 at union means 70. The union means 70 generally extends along the longitudinal centerline of the compound sanitary napkin. The compound sanitary napkin has a union means width 41, which is the distance across the union means 70. The union means width 41 may be the same or less than the width of the primary absorbent member. In a preferred embodiment, the union means 70 has a width 41 that is less than the width of the primary absorbent member in a central region of the primary absorbent member and optionally has a width that is substantially the same as the width of the primary absorbent member in the transverse end regions. In accordance with this embodiment of the invention, it has been found that having union means width 41 that is substantially the same as the width of the primary absorbent member in the transverse end regions of the compound napkin, that the stability and resistance to deformation of the compound napkin of the present invention while in use by a wearer is significantly enhanced.

Referring now to FIGS. 12–19, there are shown various patterns for forming the union means. While these Figures show a primary absorbent member having an hour glass shape, the patterns for forming the union means can be applied to the other contoured shapes previously described, provided of course that the patterns are slightly modified and adapted to fit within the periphery of the primary absorbent member. The union means width 41 is preferably less than 75% of the width of the central region of the primary absorbent member 30, more preferably the union means width 41 is less than 50% of the width of the central region of the primary absorbent member 30 and most preferably the union means width 41 is less than 25% of the width of the central region of the primary absorbent member 30. The stability of the compound napkin may be further enhanced by optionally extending the union means transversely across the end regions of the primary absorbent member as shown in FIG. 1. As shown in this embodiment, the laterally extending transverse end regions of the primary absorbent member and the secondary absorbent member are affixed together adjacent their respective laterally extending transverse ends 25 and 22. In addition, the union means may be extended longitudinally from the transverse end regions along a portion of the longitudinally extending side edges of the primary absorbent member. In accordance with this embodiment, the primary absorbent member of the compound napkin has been found to exhibit a greater resistance to rolling, twisting or bunching in the transverse end region when the extended union means is extended longitudinally along a portion of the longitudinal side edges of the primary absorbent member. It is preferred that the union means 70 be formed by affixing the primary absorbent member to the secondary absorbent member along their respective flange seals 36 as shown in FIG. 3A. In addition, when the union means is extended along the longitudinal side edges of the primary absorbent member in the transverse end regions, this portion of the compound napkin has been found to exhibit better resilience and recovery from laterally compressive forces of a user's thighs when worn. Preferably the union means extends along the longitudinal side edges of the primary absorbent member from its transverse end to a point about 0.5 mm to about 5 mm inward from the transverse end. In a most preferred embodiment, the union means affixes a portion of the flange of the primary absorbent member to a portion of the flange of the secondary absorbent member. It is preferred that the union means substantially follow the shape of the longitudinally extending side edges of the primary absorbent member, i.e. if the side edges are arcuate, then the union means are preferably substantially parallel to the arcuate side edges. The union means need not be continuous throughout the transverse end region, i.e. from one edge to an opposite edge, and is preferably in the form of a thin line of adhesive adjacent to the side edge. The union means may optionally be provided solely along the longitudinally extending side edges while the region intermediate the side edges is substantially free of any union means within the transverse end regions.

Thus to form the compound sanitary napkin of the present invention, the primary absorbent member and the secondary absorbent member are joined by union means 70. While the precise nature of the union means is not, per se, critical to the invention, it is of course important that the union means selected serves to join the primary absorbent member and the secondary absorbent member into the unitary compound sanitary napkin of the present invention with sufficient tenacity that the primary absorbent member and the secondary absorbent member do not become disconnected during use. Union means such as adhesive attachment including hot melt adhesives and pressure sensitive adhesives have been found to provide a satisfactory method of securing the primary absorbent member to the secondary absorbent member. If the nature of the components selected to construct the constituents of the compound sanitary napkin so permit, heat welding, ultrasonic welding, or a combination of both heat and ultrasonic welding can be used. In a preferred embodiment, the transverse end regions are joined by ultrasonic welding and the central region of the compound sanitary napkin is secured with a hot melt adhesive.

In accordance with one embodiment of the invention, the union means 70 is in the form of a continuous line of affixation extending substantially along the entire common length of the primary and secondary member. The union means 70 extends substantially along the longitudinal centerline of the compound sanitary napkin. In accordance with an alternative embodiment, the union means 41 may be in the form of discrete points of affixation in a spaced apart orientation. In accordance with this embodiment, the primary absorbent member may be affixed to the secondary absorbent member by union means in such a manner that the longest unattached distance between adjacent points of attachment is less than 75% of the common length. Optionally, the primary absorbent member is affixed to the secondary absorbent member by union means in such a manner that the longest unattached distance between adjacent points of attachment is less than 50% of the common length. Optionally, the primary absorbent member is affixed to the secondary absorbent member by union means in such a manner that the longest unattached distance between adjacent points of attachment is less than 25% of the common length. Optionally, the primary absorbent member is affixed to the secondary absorbent member by union means extending along substantially their entire common length. In a preferred embodiment, the union means 70 is in the form of a longitudinally extending adhesive line or stripe along the longitudinal centerline of the primary absorbent member and the secondary absorbent member wherein the width of the stripe is less than the width of the primary absorbent member. Additionally, it is preferred that the union means extend substantially across the entire width of the transverse end regions of the primary absorbent member. In a preferred embodiment, the union means extends along substantially the entire length of the primary absorbent member.

Referring again to FIG. 3C, there is shown another embodiment of the invention, wherein the primary absorbent member 30 optionally further comprises a liquid acquisition layer 46 positioned between the topsheet 32 and the absorbent core 34. The liquid acquisition layer 46 may serve several functions including improving wicking of exudates over and into the absorbent core 34. By improving the wicking of exudates, the acquisition layer provides a more even distribution of the exudates throughout the absorbent core. The acquisition layer 46 may be comprised of several different materials including nonwoven or woven webs of synthetic fibers including polyester, polypropylene, or polyethylene; natural fibers including cotton or cellulose; blends of such fibers; or any equivalent materials or combinations of materials. In a preferred embodiment, the acquisition layer 46 may be joined with the topsheet by any of the conventional means for joining webs together such as for example using adhesive, thermo-bonding techniques, and the like. In a preferred embodiment, the liquid acquisition layer 46 is a sheet of tissue or nonwoven fabric having a contoured shape wherein the transverse end regions have a width that is greater than the width in a center region. In accordance with this embodiment, the absorbent core 34 has substantially straight side edges, and the width of the liquid acquisition layer 46 is greater than the width of the absorbent core 34.

Referring again to FIGS. 1–3D, the compound sanitary napkin of the present invention further comprises a secondary absorbent member 50. The secondary absorbent member 50 preferably comprises a liquid permeable topsheet 52, a liquid impervious barrier sheet 54 joined with the topsheet 52, and may optionally include absorbent element 56, which if present would be positioned between the topsheet 52 and the barrier sheet 54.

The topsheet 52 of the secondary absorbent member 50 can be any liquid pervious material commonly used in sanitary napkins, disposable diapers, and the like and includes any of the materials described above as being useful in the topsheet 32 of the primary absorbent member 30. A preferred topsheet 52 comprises an apertured formed film. Apertured formed films are preferred for the topsheet because they are pervious to body exudates and yet non-absorbent and have a reduced tendency to allow liquids to pass back through and re-wet the wearer's skin. Thus, the surface of the formed film which is in contact with the body remains dry, thereby reducing body soiling and creating a more comfortable feel for the wearer.

The absorbent element 56 can be any absorbent material commonly used in sanitary napkins, disposable diapers, and the like and can be any of the materials described above as being useful in the absorbent structure 33 and/or absorbent core 34 of the primary absorbent member 30. However, since the absorbent core 34 of the primary absorbent member is adapted to absorb and contain most of the bodily liquids, a major function of the secondary absorbent member 50 is to protect the user's garments from soiling by absorbed liquids which may be expelled from the primary absorbent member or which may inadvertently bypass the primary absorbent member. Because the absorbent core 34 is preferably intended to absorb most or substantially all of the bodily liquids during use, its absorptive capacity is preferably somewhat if not significantly greater than that of the absorbent element 56 and the absorbent element 56 can be, and most preferably is, somewhat thinner, less bulky, and/or formed of materials having less absorptive capacity than the absorbent core 34. Thus, in accordance with an optional embodiment of the present invention, the overall absorptive capacity of the absorbent element 56 is somewhat less than that of the absorbent core 34. For example, single or multiple plies of paper tissue as commonly used in paper toweling or toilet tissue can be used to form the absorbent element 56. Preferably, the absorbent element 56 is formed of from about 1 to about 5 plies of paper tissue. Paper tissue comprising one or more plies having a basis weight of from about 24 to about 48 grams per square meter and an apparent density of from about 0.10 to about 0.12 grams per cubic centimeter has been found to be quite satisfactory for use as the absorbent element 56. Wet strength resins and latex binders can be, and preferably are, used to provide additional strength to the paper tissue used in the absorbent element 56.

The secondary absorbent member may be manufactured with or without an absorbent element 56. Since most if not all of the bodily liquids are preferably absorbed by and are contained within the absorbent core of the primary absorbent member, the secondary absorbent member 50 need only to protect the user's garments from soiling by relatively small amounts of liquids which may be expelled from the primary absorbent member or which may inadvertently bypass the primary absorbent member. Accordingly, since only relatively small amounts of liquids are expected to come into contact with the secondary absorbent, an absorbent element 56 may not be necessary to contain the liquids within the secondary absorbent member and prevent them from soiling the user's garments.

The barrier sheet 54 is constructed of flexible materials that are impervious to liquids (e.g., menses and/or urine) to prevent exudates which may be expelled from or which inadvertently bypass the primary absorbent member and exudates absorbed and contained in the absorbent element 56 from contacting and soiling the user's undergarments. In use, the barrier sheet 54 is interposed between the absorbent element 56 and the user's undergarments. As used herein, the term "flexible" refers to materials which are soft, compliant and will readily conform to the general shape and contours of the human body. The barrier sheet 54 may thus comprise a woven or nonwoven fabric material that has been treated to make it liquid impervious, a thin polymeric film such as thermoplastic films of polyethylene or polypropylene, or composite materials such as a film-coated nonwoven material. Preferably, the barrier sheet is a polyethylene film having a thickness of from about 0.012 mm (0.5 mil) to about 0.015 mm (2.0 mil). Exemplary polyethylene films are manufactured by Clopay Plastic Products Co. having an address at 312 Walnut St Cincinnati, Ohio 45202, Huntsman Packaging having an address at 230 Enterprise Drive, Newport News, Va. 23603, Tredegar Industries having an address at 1100 Boulders Parkway, Richmond, Va. 23225, Exxon Chemical Co. having an address at 750 West Lake Cook Road, Buffalo Grove, Ill. 60089. The barrier sheet is preferably embossed and/or matte finished to provide a more cloth-like appearance. Further, the barrier sheet may permit vapors to escape from the absorbent element 56 (i.e., breathable) while still preventing exudates from passing through the barrier sheet.

Preferably, the secondary absorbent member 50 is provided with an attachment means, such as adhesive attachment means 58 for securing the compound sanitary napkin 20 in the crotch portion of the user's undergarment. Thus, a portion or all of the outer or garment surface 55 of the barrier sheet 54 is coated with adhesive. In a preferred embodiment, at least a portion of the adhesive 58 is positioned on the garment surface 55 of the barrier sheet 54 adjacent the longitudinal side edges 21 of the secondary absorbent member. Any adhesive or glue used in the art for such purposes can be used for the adhesive herein, with pressure-sensitive adhesives being preferred. Suitable adhesives include hot melt adhesives such as HL 1417xzp adhesive and HL 1491xzp adhesive which are commercially available from HB Fuller Corporation St. Paul, Minn. 55110 or H2262 adhesive and H2543 adhesive which are commercially available from ATO Findley Inc. Wauwatosa, Wis. 53226. The pressure-sensitive adhesive is typically covered with a removable release liner 59 in order to keep the adhesive from drying out or adhering to a surface other than the crotch portion of the undergarment prior to use. Any commercially available release liners commonly used for such purposes can be utilized herein. A suitable release liner is commercially available from Tekkote Corporation, Leonia, N.J. 07605. The compound sanitary napkin 20 of the present invention is used by removing the release liner 50 and thereafter placing the sanitary napkin in an undergarment so that the adhesive 58 contacts the undergarment. The adhesive 58 maintains the sanitary napkin in its position within the undergarment during use.

The secondary absorbent member of the present invention is preferably relatively thin and flexible. Preferably, the secondary absorbent member will have a caliper of less than about 3.0 millimeters, more preferably less than about 2.6 millimeters, more preferably less than about 2.2 millimeters, and most preferably less than about 2.0 millimeters. The caliper of the compound sanitary napkin, the primary absorbent member or the secondary absorbent member, including various regions thereof, may conveniently be determined by the following test. A comparator gauge, and specifically the Ames, Model 130 with dial indicator Model 482, available from the B. C. Ames Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the absorbent member (with any undergarment adhesive release paper being removed and adhesive sprinkled with corn starch) is placed garment surface down on the base plate. The absorbent member is positioned on the base plate so that when the foot is lowered it is in the region of the absorbent member for which the measurement is desired. The surface of the absorbent member being evaluated should be smooth and any wrinkles in the absorbent member should be avoided. The foot should be gently lowered onto the secondary absorbent member and the caliper determined by reading the comparator dial 30 seconds after the foot comes in contact with the absorbent member.

Referring again to FIG. 1, the secondary absorbent member 50 preferably has a length 60 and a width 61. The secondary absorbent member is preferably from about 20 to 40 cm long, more preferably from about 25 to 35 cm long, and most preferably is about 30 cm long. The average crotch width of an undergarment generally ranges from about 4 cm to about 9 cm and the average groin width generally ranges from about 1 cm to about 4 cm and accordingly the width dimensions of the primary absorbent member and secondary absorbent member will correspond to these dimensions. While it can be of generally any cross-section in its unstressed condition, the absorbent element 56 # within the secondary absorbent member preferably has a width of from about 5 to 15 cm, more preferably from about 5 to 10 cm, and most preferably from about 5 to 8 cm. In this embodiment of the invention, the primary absorbent member 30 and the secondary absorbent member 50 have a common length 65 and a common width in the end regions 27 and 29.

The thickness of the secondary absorbent member 50, as shown in cross-section in FIGS. 2 and 3A–C, is substantially less than its width. Because the primary absorbent member performs different functions than that of the secondary absorbent member, the dimensions, properties and characteristics of the materials forming the primary absorbent member and a secondary absorbent member may be distinct from one another. One major function of the primary absorbent member is to absorb and contain bodily liquids. In addition, the primary member is preferably sized and shaped such that it comfortably fits within the user's groin region. Accordingly, the combination of width and caliper (and/or diameter) of the primary absorbent member in a center region should be sized such that it will reside comfortably within the user's groin region. In a preferred embodiment, the center region of the primary absorbent member is sized and configured to comfortably reside and contact the user's groin along the entire length of the groin. As used herein, the terminology "length of groin" refers to the groin region between the user's legs. Optionally, a portion of the primary absorbent member may fit within the labia during use. In a preferred embodiment, the combination of width and caliper (and/or diameter) of the primary absorbent member has a volume that is sufficient to maintain contact with at least a portion of the user's groin region in use and to gently compress the user's labia majora. Since the exposed female genitalia, including the labia, are generally referred to as soft body tissue, it is important that the materials comprising and the primary absorbent member be comfortable and relatively soft such that they are non-irritating and/or uncomfortable for the user. In contrast, one major function of the secondary absorbent member is to protect the user's garments from soiling by absorbed liquids which may be expelled from the primary absorbent member or which may inadvertently bypass the primary absorbent member.

Preferably, the width of the secondary absorbent member in the central region is at least 1.5 times the width of the primary absorbent member in the central region. More preferably, the width of the secondary absorbent member in the central region is at least 2 times the width of the primary absorbent member in the central region. Most preferably, the width of the secondary absorbent member in the central region is in the range from about 3 to about 8 times the width of the primary absorbent member in the central region. Preferably, the secondary absorbent member is about the same length as the primary absorbent member while the compound sanitary napkin is in an unstressed condition. However, it is quite possible for the secondary absorbent member to be somewhat longer than the primary absorbent member and still function effectively.

As shown in FIGS. 1–3, the compound sanitary napkin 30 has a first end region 27, a central region 28, and a second end region 29, wherein the primary absorbent member has a relatively narrow width in the central region and a relatively wider width in at least one of the transverse end regions. While the secondary absorbent member is shown has a generally rectangular shape, other suitable shapes for the secondary absorbent member include but are not limited to oval, hourglass, dog-bone, asymmetric, etc.

Figure 20:
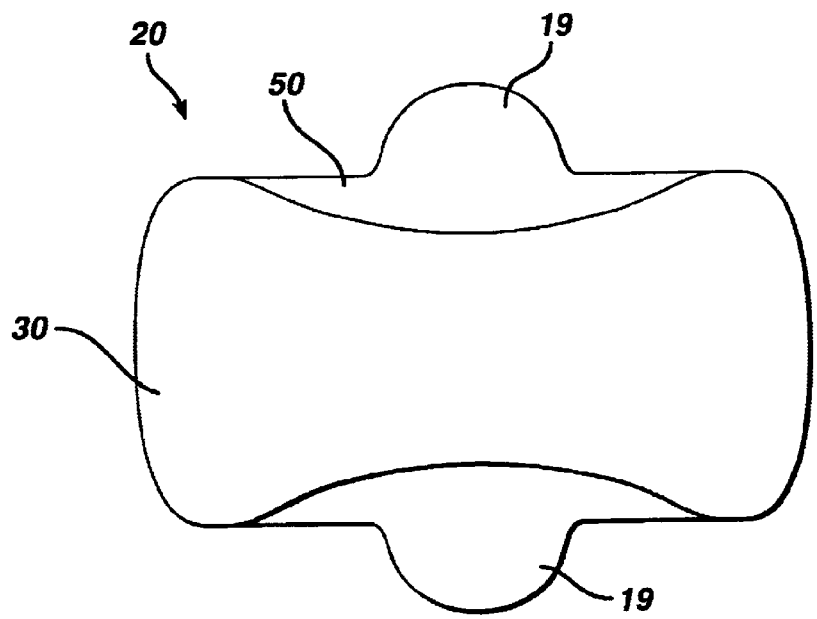
FIG. 20 is a top plan view of another embodiment of the compound sanitary napkin of the present invention.
Figure 21:
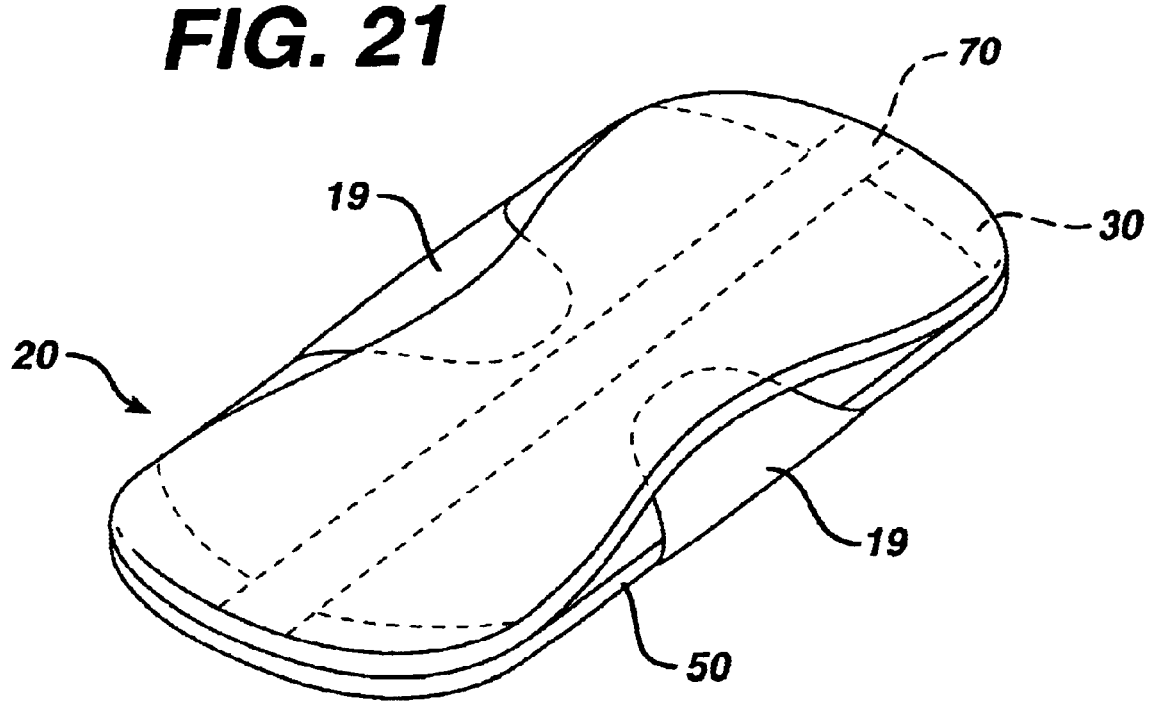
FIG. 21 is a top plan view of another embodiment of the compound sanitary napkin of the present invention.

Referring now to FIGS. 20 and 21, there is shown another preferred embodiment of the invention is illustrated wherein the compound napkin is provided with two side flaps 19. In accordance with this embodiment, the two side flaps 19 are adjacent to and extend laterally from the side edges of the absorbent element 56 of the secondary absorbent member 50. The flaps 19 are flexible and configured to be folded over the edges of the wearer's panties in the crotch region so that the flaps are disposed between the edges of the wearer's panties and the wearer's thighs. The flaps serve at least two purposes; first to prevent soiling of the wearer's body and panties by menstrual liquid, preferably by forming a double wall barrier along the edges of the undergarment, and second, the flaps are provided with attachment means on their garment facing surface so that the flaps can be folded back under the undergarment and attached to the garment facing side of the undergarment to keep the sanitary napkin properly positioned in the undergarment.

In a most preferred embodiment, the flaps are comprised of a laminate of integral and contiguous extensions of the topsheet and barrier sheet of the secondary absorbent member. In accordance with this embodiment, the topsheet and barrier sheet simply extend laterally outward from the edge of the absorbent element 56 (not shown) to form the flaps. However, the flaps need not be unitary with the secondary absorbent member, and may be separate elements which are affixed to the secondary absorbent member. Further, the flaps can be comprised of a single substrate or other laminae configurations. It is preferred, however, that the flaps have a liquid impervious barrier sheet to prevent exudates which reach the flaps from soiling the edges of the wearer's panties.

Further, the flaps may optionally be provided with a thin layer of absorbent material, preferably extending laterally outward from the longitudinal side edges in an amount sufficient that when placed in a crotch region of an undergarment, the thin layer of absorbent material extends beyond the edges of the wearer's panties. Theoretically, only a relatively small amount of menses should reach the flaps, therefore, only a relatively small amount of absorbent material is desirable in the flaps in an amount sufficient to prevent any exudates that reach the flaps from being able to flow further to unprotected areas. The absorbent material may be a tissue, or a relatively thinner extension of the absorbent element 56. However, the absorbent material in the flaps should be relatively highly flexible.

A number of sanitary napkins having flaps suitable or adaptable for use with the secondary absorbent member 50 of the compound sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986. Each of these patents are incorporated herein by reference in their entirety.

The flaps are preferably folded over the topsheet of either the secondary absorbent member or both the secondary absorbent member and the primary absorbent member. More particularly, each flap has a proximal end that is coincident with the longitudinal side edges of the secondary absorbent member and a freely extending distal end opposite the proximal end. In accordance with this embodiment, the distal ends are folded over the topsheet in a facing relationship. In a most preferred embodiment, the flaps preferably have an attachment means such as adhesive on a garment facing side thereof that is adapted to releasably affix the flaps to an underside of the undergarment in use. The distal ends of the flaps are folded over the topsheet of the secondary absorbent member and preferably releasably secured in this orientation prior to use by a wearer of the compound sanitary napkin. One method for releasably securing the flaps in the folded orientation is by a single strip of release paper that extends from one flap across the topsheet of the compound napkin to the opposite flap and is releasably affixed to the adhesive on the garment facing side of the flaps. Alternatively as shown in FIG. 21, the flaps may be folded over the topsheet of the secondary absorbent member such that the distal ends of the flaps are inserted between the primary absorbent member and the secondary absorbent member in the region intermediate the union means and the longitudinal side edge of the primary absorbent member. Thus, in accordance with this embodiment, the union means in a central region of the primary absorbent member has a width that is less than the width of the primary absorbent member. Since the union means is located inward from the longitudinal side edges of the primary absorbent member, there exists an unaffixed region in the form of a pocket between the primary absorbent member and the secondary absorbent member. The distal ends of the flaps may be inserted into this region or pocket between the primary absorbent member and the secondary absorbent member and maintained in this orientation prior to use by a wearer of the compound sanitary napkin. Depending of course on the length of the flaps (as measured between the proximal end and the distal end) it may be advantageous to form a second fold (not shown) within the body of the flap and to insert this second folded region between the primary absorbent member and the secondary member.

The individual components of the primary absorbent member 30 and/or the secondary absorbent member 50 may be comprised of components that are extensible (preferably, capable of stretching) particularly in the longitudinal direction when the compound sanitary napkin is worn. Preferably, the compound sanitary napkin is capable of elongating in the longitudinal direction between about 15% and about 40% of its unstretched length. This extensibility provide better in-use fit, comfort, and decreased staining when the compound sanitary napkin is affixed to the wearer's undergarments.

Preferably, the secondary absorbent member is comprised of components that are also extensible in the lateral direction when the compound sanitary napkin is worn. Preferably, the compound sanitary napkin is capable of elongating in the lateral direction between about 15% and about 40% of its unstretched length. The topsheet for both the primary absorbent member and the secondary absorbent member may comprise an elastic, three-dimensional, liquid pervious, polymeric web.

Figure 22:
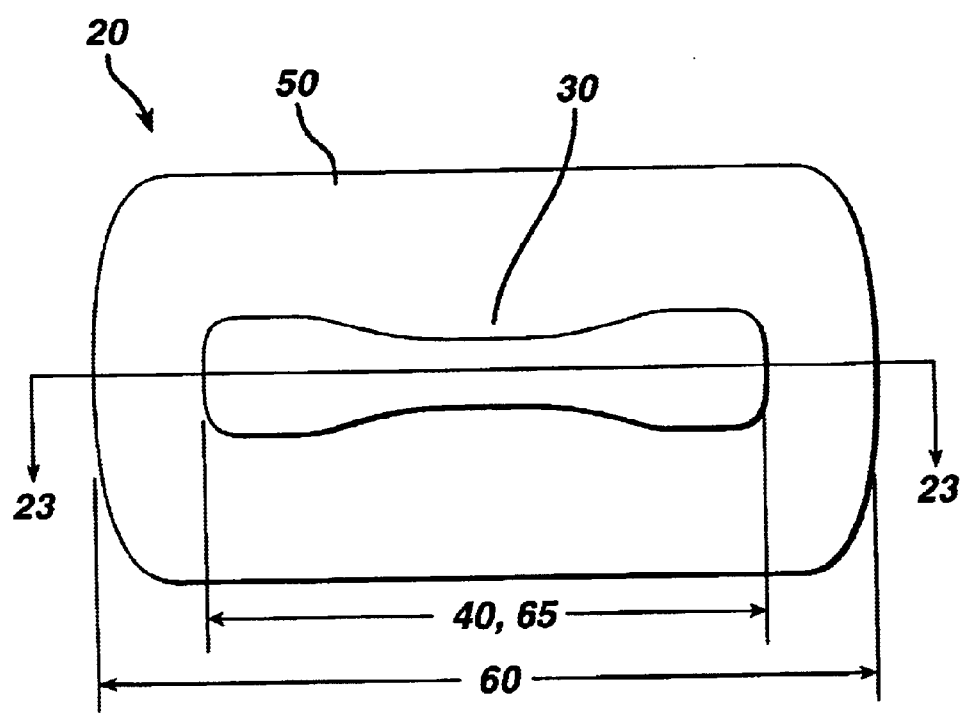
FIG. 22 is a top plan view of another embodiment of the compound sanitary napkin of the present invention.
Figure 23:
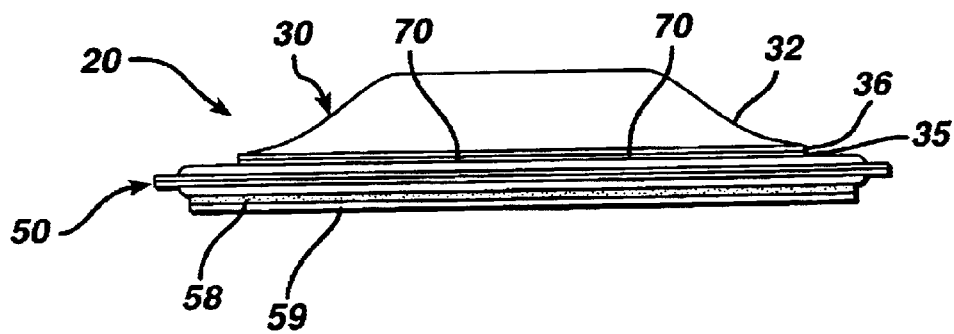
FIG. 23 is a side elevation view of the compound sanitary napkin shown in FIG. 22 as taken along section lines 23—23.

Referring now to FIGS. 22 and 23, there is shown another preferred embodiment of a compound sanitary napkin 20 of the present invention wherein the primary absorbent member 30 and the secondary absorbent member 50 have different lengths and widths. The primary absorbent member 30 has a length 40 that is somewhat less than the length 60 of the secondary absorbent member 50 and the width of the primary absorbent member 30 in the transverse end regions as well as the central region is less than the width of the secondary absorbent member 50 in each of these respective regions.

Figure 24:
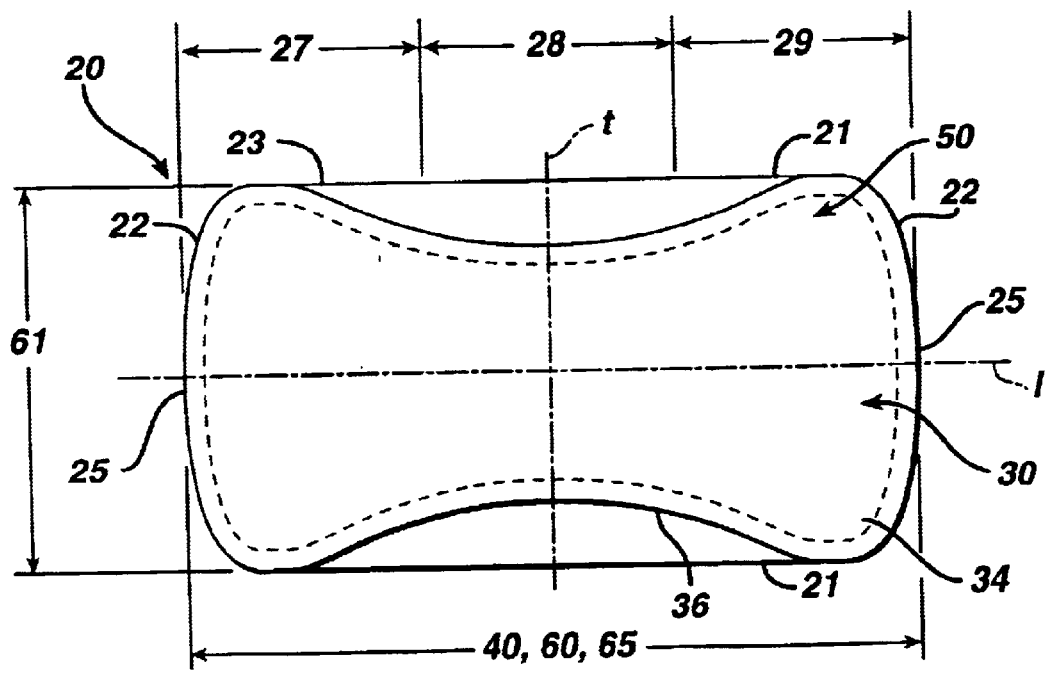
FIG. 24 is a top plan view of another embodiment of the compound sanitary napkin of the present invention.

Referring to FIG. 24, there is illustrated another preferred embodiment of the invention wherein the primary absorbent member 30 has absorbent core 34 in the shape of an hourglass. The length of the absorbent core 34 is less than the length 40 of the primary absorbent member 30 and the width of the absorbent core 34 is less than the width of the primary absorbent member 30. It is preferred that the width of the primary absorbent member 30 in the transverse end regions 27 and 29 have a common width (i.e. be co-extensive) with the secondary absorbent member 50 in its respective transverse end regions. The topsheet 34 and the barrier layer (not shown) are sealed together around their respective outer peripheral edge margins to form flange seal 36.

Figure 25:
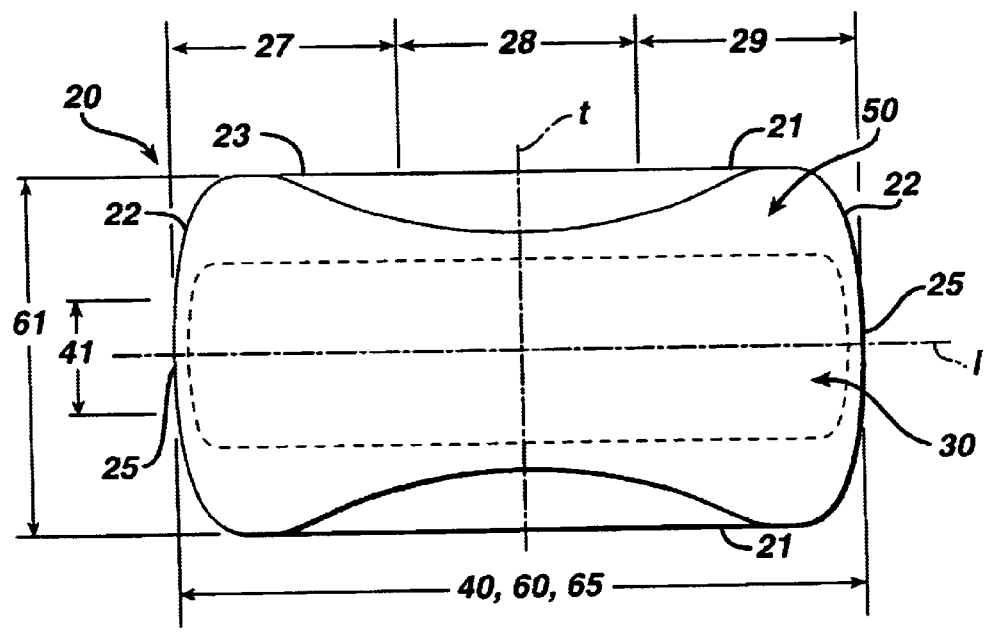
FIG. 25 is a top plan view of another embodiment of the compound sanitary napkin of the present invention.

Referring to FIG. 25, the primary absorbent member 30 has a substantially rectangular shaped absorbent core 34 having a width 41 which is substantially less than the width of the primary absorbent member 30 having longitudinally extending peripheral regions which are substantially free of absorbent material and which have increased flexibility relative to the longitudinally extending centrally located absorbent core. In accordance with this embodiment of the invention, the primary absorbent member 30 includes the topsheet and backsheet and centrally located absorbent core 34. The primary absorbent member may optionally include a layer of tissue or non-woven fabric (not shown) which extends beyond the longitudinally extending edges of the absorbent core into the longitudinally extending peripheral regions. The tissue or non-woven fabric is preferably shaped similarly to the primary absorbent member 30, i.e. hourglass shaped and is adapted to preferentially wick absorbed fluid within the plane of the tissue or non-woven fabric to aid in distributing the fluid throughout the primary absorbent member.

Figure 26:
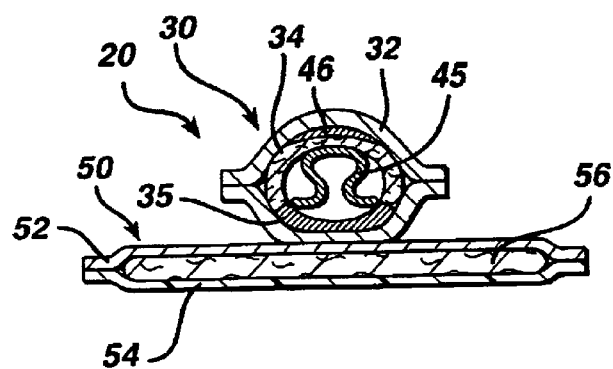
FIG. 26 is a cross-sectional view of another embodiment of a compound sanitary napkin of the present invention.

Several specific non-limiting embodiments of the compound sanitary napkins of the present invention are shown in FIGS. 26–36. An example of a primary absorbent member having a Z-folded resilient member 45 is shown in FIG. 26. In accordance with this embodiment, the absorbent core 34 is positioned between the topsheet 100 and the resilient member 45 of the primary absorbent member 30. The resilient member 45 has a substantially U-shaped cross-section and causes the primary absorbent member 30 to have a generally U-shaped cross-section. The resiliency of the resilient member 45 is preferably not affected by the presence of body exudates absorbed by and contained within the absorbent core. The sustained resiliency of the resilient member 45 permits the primary absorbent member 30 to maintain intimate contact with the body of the wearer during use. Positioning the absorbent core 34 between the topsheet 32 and the resilient member 45 helps to provide intimate contact between the absorbent core 34 and the topsheet 32. Intimate contact between the topsheet and the absorbent core through bonding or pressure applied by the resilient member is described to promote liquid transfer from the topsheet into the underlying absorbent core.

Figure 27:
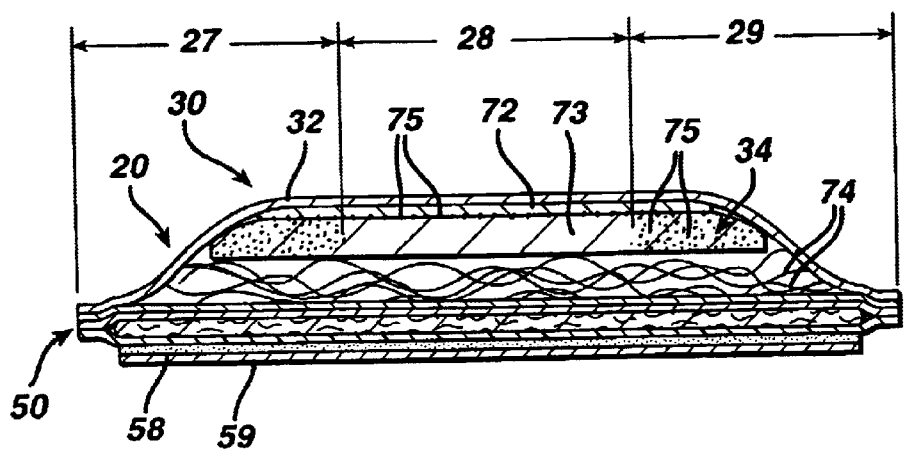
FIG. 27 is a cross-sectional view taken along the longitudinal axis of another embodiment of a compound sanitary napkin of the present invention.

Referring now to FIG. 27 there is shown a cross-sectional view taken along the longitudinal axis of another embodiment of a compound sanitary napkin 20 of the present invention. The primary absorbent member 30 includes an absorbent core 34 comprised of a relatively low density layer 72, a relatively high density layer 73, a plurality of resilient fibers 74, and absorbent gelling material 75 dispersed on and within the high density layer 73. The absorbent gelling material 75 is dispersed primarily within the first and second end regions 27, 29 of the primary absorbent member 30. The relatively low density layer 72 is preferably comprised of a thermally bonded airlaid material. The relatively high density layer 73 is preferably comprised of a thermally bonded airlaid material. The resilient fibers are preferably polyester capillary channel fibers.

Figure 28:
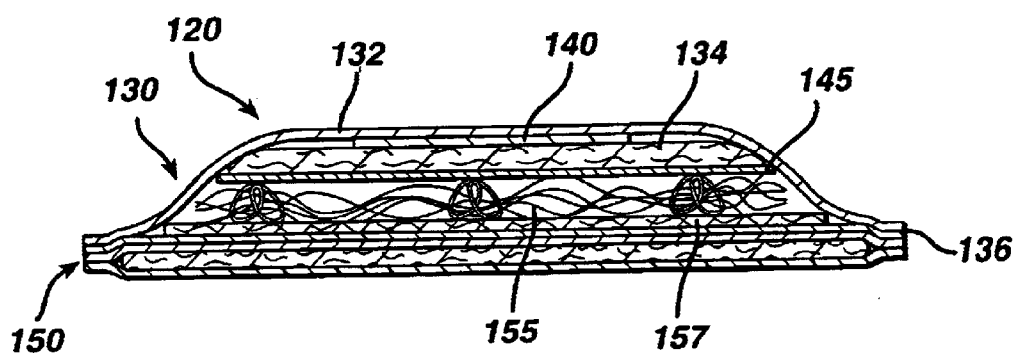
FIG. 28 is a cross-sectional view taken along the longitudinal axis of another embodiment of a compound sanitary napkin of the present invention.

Referring to FIG. 28, there is shown another embodiment of a compound sanitary napkin 120. The compound sanitary napkin 120 comprises a primary absorbent member 130 and a secondary absorbent member 150. The primary absorbent member 130 includes an apertured formed film topsheet 132, an acquisition element 140, a distribution element 145, absorbent core layer 150, a first resilient member 155, second resilient member 157 and barrier layer 135. The topsheet 132 and barrier layer 135 are sealed together along their respective outer peripheral edge margins to form flange seal 136 to fully enclose absorbent core layer 150, first resilient member 155 and second resilient member 157. The first resilient member 155 extends substantially throughout the length of the primary absorbent member 130. The first resilient member 155 preferably comprises polymeric capillary channel fibers. The second resilient member 157 preferably comprises nylon mono-filament arranged in a substantially circular cross-section secured to one another near the acquisition element 140 and near the interior surface of the absorbent core 150. As can be seen in FIG. 28, the secondary resilient members 157 are positioned substantially in the central region of the primary absorbent member 130.

Figure 12:
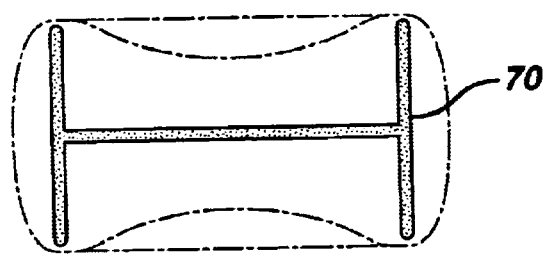
FIG. 12 is a top plan view of one embodiment of the compound sanitary napkin of the present invention.
Figure 29:
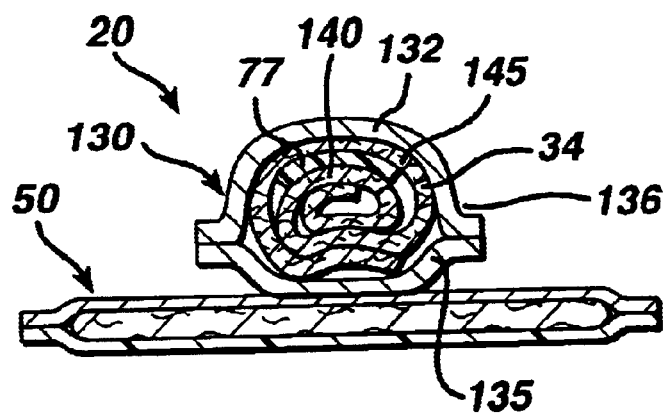
FIG. 29 is a cross-sectional view of another embodiment of a compound sanitary napkin of the present invention.

Referring to FIG. 29, there is shown a cross-sectional view of another embodiment of a compound sanitary napkin 20 of the present invention. The absorbent core 34 comprises a carded nonwoven layer of capillary channel fibers. The nonwoven layer is rolled onto itself to form multiple layers. Preferably, a masking element 77 is positioned within the nonwoven layer of capillary channel fibers. A suitable masking element is a liquid impervious film. Another suitable masking element is a formed film. Optionally, absorbent materials such as absorbent gelling materials may be incorporated into the nonwoven layer of capillary channel fibers. While the nonwoven layer of capillary channel fibers is shown in FIG. 12 as having a generally circular cross-section, the layer of capillary channel fibers may be manufactured in a wide variety of shapes such as rectangular, triangular, oval, U-shaped, Z-folded, etc.

Figure 13:
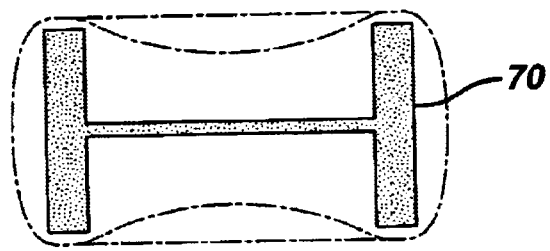
FIG. 13 is a top plan view of one embodiment of the compound sanitary napkin of the present invention.
Figure 14:
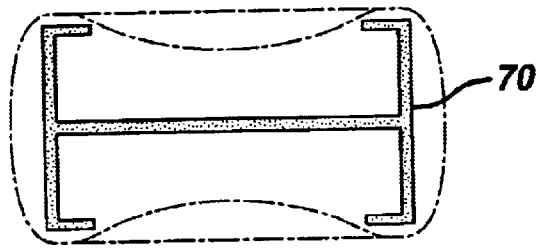
FIG. 14 is a top plan view of one embodiment of the compound sanitary napkin of the present invention.
Figure 15:
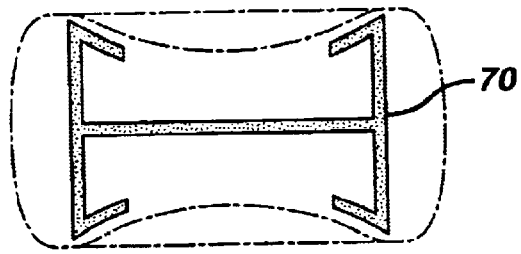
FIG. 15 is a top plan view of one embodiment of the compound sanitary napkin of the present invention.
Figure 16:
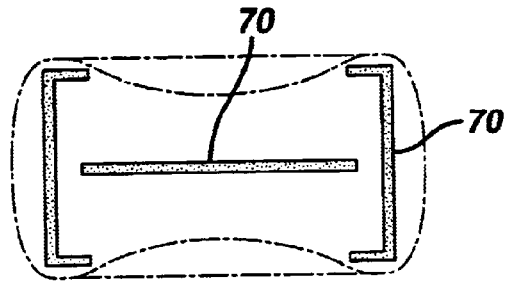
FIG. 16 is a top plan view of one embodiment of the compound sanitary napkin of the present invention.
Figure 17:
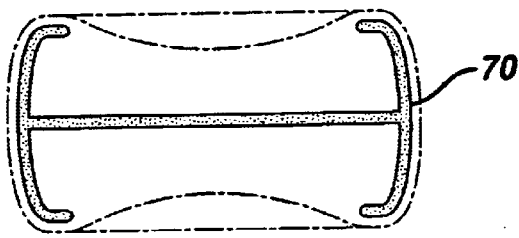
FIG. 17 is a top plan view of one embodiment of the compound sanitary napkin of the present invention.
Figure 18:
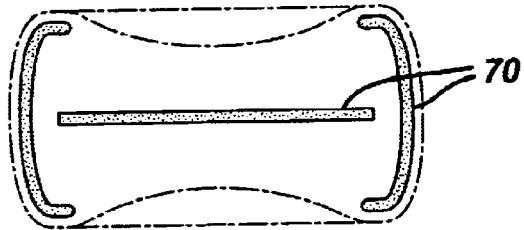
FIG. 18 is a top plan view of one embodiment of the compound sanitary napkin of the present invention.
Figure 19:
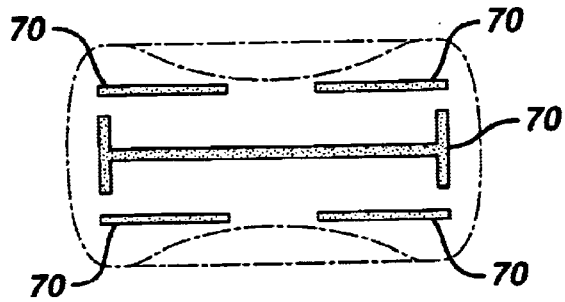
FIG. 19 is a top plan view of one embodiment of the compound sanitary napkin of the present invention.
Figure 30:
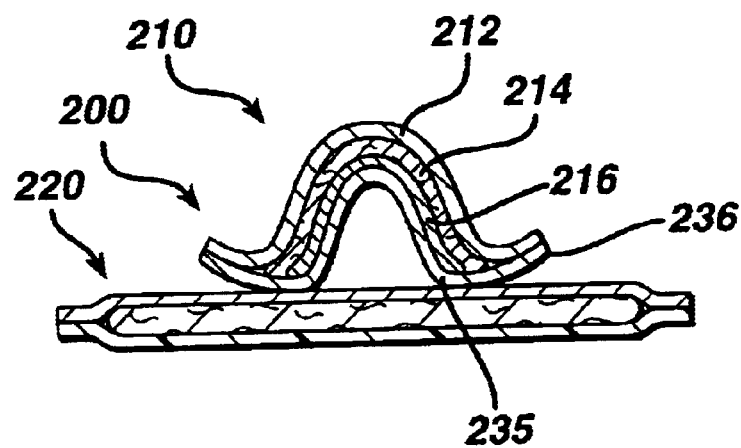
FIG. 30 is a cross-sectional view of another embodiment of a compound sanitary napkin of the present invention.

Referring to FIG. 30, there is shown another preferred embodiment of a compound sanitary napkin 200. The compound sanitary napkin 200 comprises a primary absorbent member 210 and a secondary absorbent member 220. The primary absorbent member 210 preferably comprises a topsheet 212, an absorbent core 214, a resilient member 216 and a barrier layer 235. As can be seen in FIG. 13, the resilient member 216 has a substantially inverted U-shaped cross-section. Accordingly, the primary absorbent member 210 likewise has a substantially inverted U-shaped cross-section. Preferably, the resilient member 216 extends throughout substantially the entire length of the primary absorbent member 210. The topsheet 212 and barrier layer 235 are sealed together along their respective outer peripheral edge margins to form flange seal 236 to fully enclose absorbent core 214 and resilient member 216.

Figure 31:
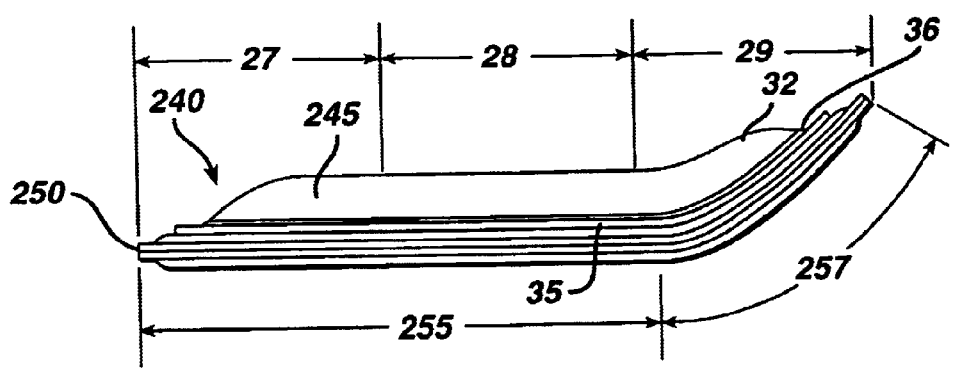
FIG. 31 is a side elevational view of another embodiment of a compound sanitary napkin of the present invention.

Referring to FIG. 31 there is shown another preferred embodiment of a compound sanitary napkin 240 of the present invention. Compound sanitary napkin 240 preferably comprises a primary absorbent member 245 having a topsheet 32, barrier sheet 35 which are sealed about their peripheral edge margins to form flange seal 36 and a secondary absorbent member 250. As can be seen in FIG. 31 the compound sanitary napkin 240 preferably has a substantially horizontal segment 255 and an upwardly curved segment 257. The horizontal segment 255 resides within first end region 27 and central region 28. Upwardly curved segment 257 resides within second end region 29. Preferably, the upwardly curved segment 257 includes a tensioning means which provides ample tension to create the curvature in the second segment 257. Suitable tensioning means include but are not limited to a tensioned topsheet, an elastic material, thread, film, or any suitable means to provide the desired tension. Optionally, the segment residing within the first end region 27 may also be upwardly curved.

Figure 32:
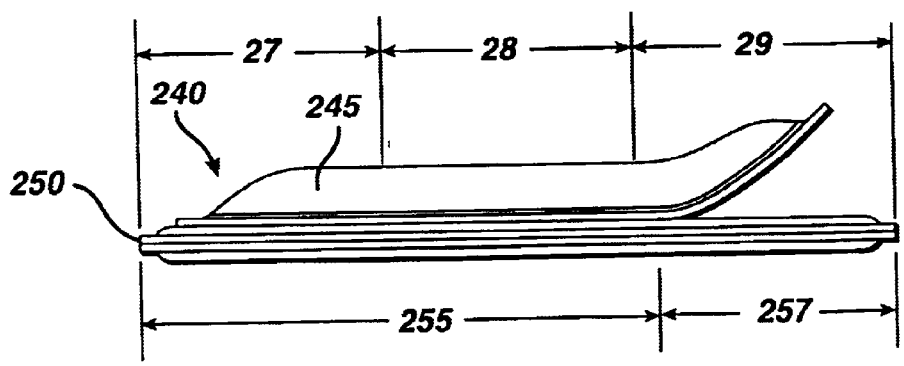
FIG. 32 is a side elevation view of another embodiment of a compound sanitary napkin.

As seen in FIG. 31 the primary absorbent member 245 and the secondary absorbent member 250 are joined together throughout their entire common length. That is, they are joined together throughout segments 255 and 257. Optionally, they may be joined together in the first segment 255 and may separate from one another in the rear segment 257 as shown in FIG. 32. In this embodiment, the secondary absorbent member 250 remains substantially in the same plane throughout segments 255 and 257 while in an unstressed condition. The primary absorbent member 245 positioned within the second segment 257 curves upward away from and separates itself from the secondary absorbent member 250. The segment 257 generally corresponds with the second end region 29. The primary absorbent member may also curve upwardly within the first end region 27.

Figure 33:
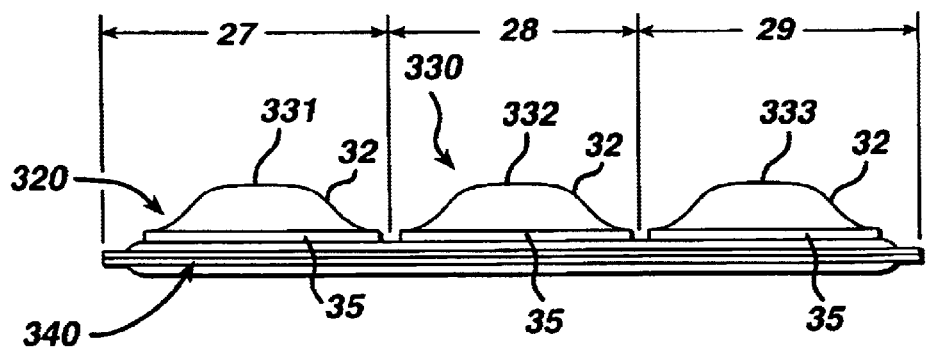
FIG. 33 is a side elevational view of another embodiment of a compound sanitary napkin of the present invention.
Figure 34:
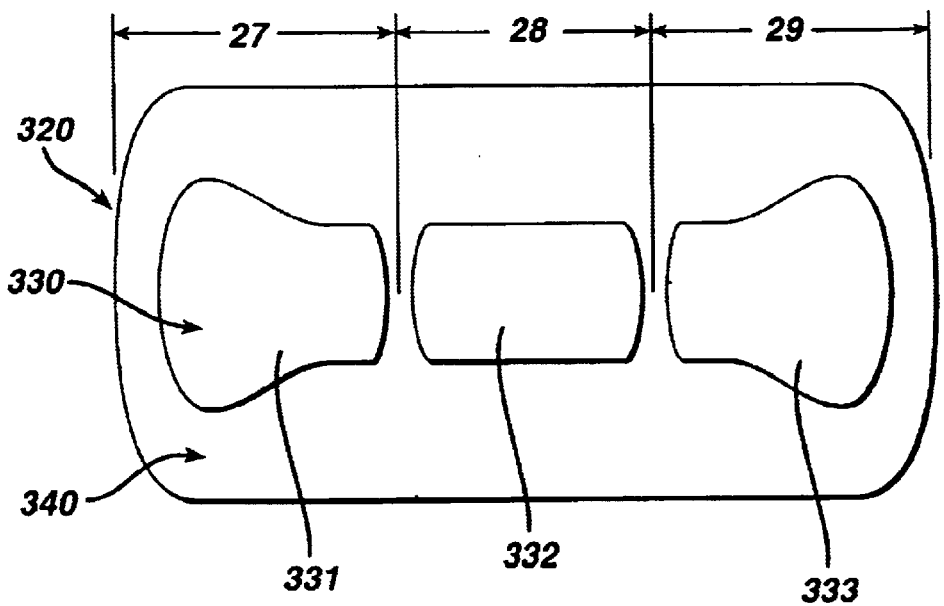
FIG. 34 is a top plan view of another embodiment of a compound sanitary napkin of the present invention.
Figure 35:
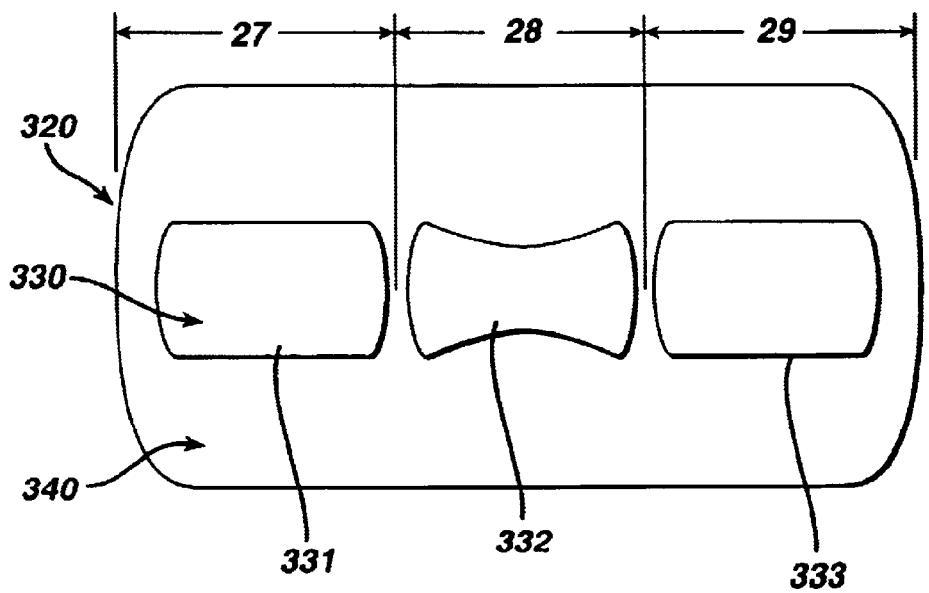
FIG. 35 is a top plan view of another embodiment of a compound sanitary napkin of the present invention.

Referring to FIGS. 33 and 34, there is shown another embodiment of the compound sanitary napkin 320 of the present invention. In accordance with this embodiment, the compound sanitary napkin 320 comprises a segmented primary absorbent member 330 and a secondary absorbent member 340. The primary absorbent member comprises individual absorbent components 331, 332 and 333, which together define a primary absorbent member having a relatively narrow central region and relatively wider transverse end regions. As shown in FIGS. 33, 34 and 35, segment 331 lies wholly within first end region 27, segment 332 is narrower in width than segment 331 or segment 333 and resides wholly within central region 28, and segment 333 resides wholly within second end region 39. Optionally, the primary absorbent member may comprise two components which extend from the end regions 27 and 29 into the central region 28. Optionally, the primary absorbent member may be comprised of 4 or more individual components. While the primary absorbent member having multiple components is shown in FIGS. 33 and 34 as extending throughout the length of the compound sanitary napkin, it may be desirable to have some segments or some regions of the compound sanitary napkin having no primary absorbent member. For example, the first end region 27 and central region 28 may comprise an primary absorbent constituent where second end region 29 comprises only a secondary absorbent member. Moreover, the primary absorbent members within the various regions may be designed to perform specific functions and therefore may be made of materials to perform the desired functions. For example, the primary absorbent segment 332 within central region 28 may contain a greater capacity of absorbent material than that of segments 331 or segments 333 since segment 332 will likely be positioned such that it will receive the bodily liquids directly, whereas the elements or segment 331 or 333 will likely receive and therefore have less capacity than that of the segment 332 within central region 28.

FIG. 35 illustrates yet another embodiment of the invention. In accordance with this embodiment, the compound sanitary napkin 320 comprises a segmented primary absorbent member 330 and a secondary absorbent member 340. The primary absorbent member comprises individual absorbent components 331, 332 and 333. The centrally located segment 332 has a contoured shape having a relatively narrow central region and relatively wider transverse end regions. The absorbent segments 331 and 333 have a width that is substantially equal to the width of the transverse end regions of the central absorbent segment 332.

Figure 36:
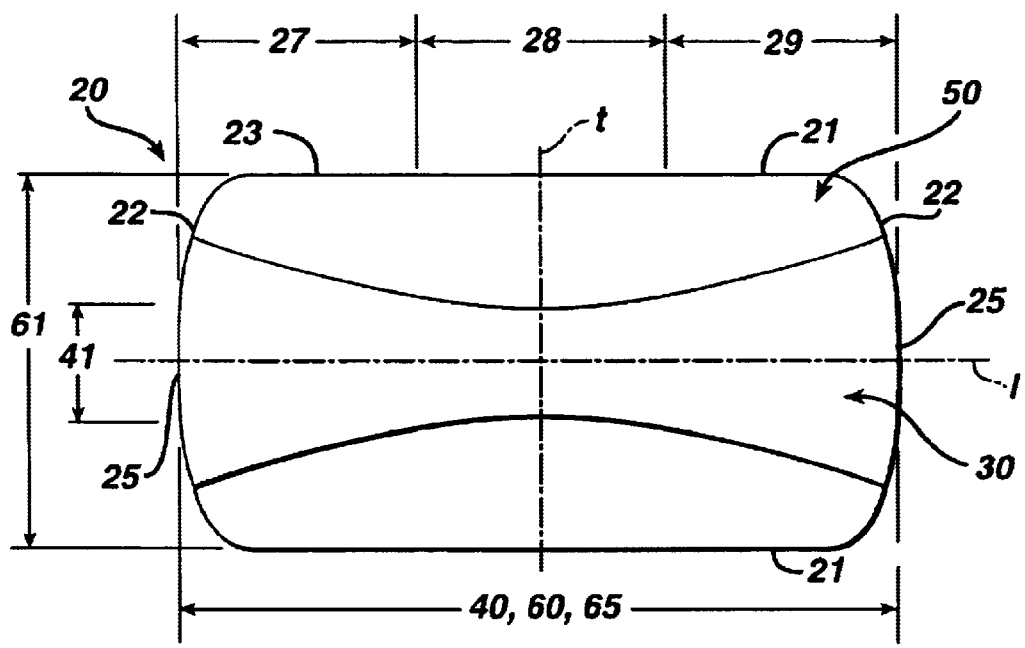
FIG. 36 is a top plan view of another embodiment of a compound sanitary napkin of the present invention.

FIGS. 8 and 36 illustrate another embodiment of the present invention. In accordance with this embodiment, the primary absorbent member has a common length with the secondary absorbent member and the transverse end regions of the primary absorbent member have a width that is less than the width of the transverse end regions of the secondary absorbent member.

It may be desirable to provide a compound sanitary napkin having a primary absorbent member with varying degrees of caliper throughout its length. For example, the primary absorbent member may be relatively thicker in the central region as opposed to the end regions. Alternatively, the primary absorbent member may be relatively thinner in the central region as opposed to the end regions.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A compound sanitary napkin adapted to be worn by a user in a crotch portion of an undergarment comprising:

an uppermost primary absorbent member and a lowermost secondary absorbent member;

the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent element between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member has a substantially hour-glass shape wherein both transverse end regions are wider than the central region and wherein the longitudinal sides are arcuate.

2. The sanitary napkin according to claim 1 wherein the secondary absorbent member has a first transverse end and an opposite transverse end defining therebetween a length and wherein the primary absorbent member and the secondary absorbent member have a common length.

3. The sanitary napkin according to claim 1 wherein the backsheet is a liquid impervious flexible sheet and the topsheet and the backsheet of the primary absorbent member are joined around a peripheral edge margin to form a flange seal which encloses the absorbent core.

4. The sanitary napkin according to claim 1 wherein the primary absorbent member has a length that is shorter than the length of the secondary absorbent member.

5. The sanitary napkin according to claim 1 wherein the width of the primary absorbent member in the center region is from about 10 mm to 65 mm and the width at the transverse ends is from about 20 mm to 85 mm.

6. The sanitary napkin according to claim 1 wherein the length of the primary absorbent member is from about 2 cm to 35 cm.

7. The sanitary napkin according to claim 1 wherein the length of the primary absorbent member is from about 10 cm to 35 cm.

8. The sanitary napkin according to claim 1 wherein the length of the primary absorbent member is from about 20 cm to 24 cm.

9. The sanitary napkin according to claim 1 wherein the topsheet of the primary absorbent member is selected from the group consisting of woven fabrics, nonwoven fabrics, apertured formed thermoplastic films, apertured plastic films, hydroformed thermoplastic films, porous foams; reticulated foams, reticulated thermoplastic films and thermoplastic scrims.

10. The sanitary napkin according to claim 9 wherein the nonwoven fabrics are comprised of materials selected from the group consisting of natural fibers, polyester fibers, polypropylene fibers, polyethylene fibers and combinations thereof.

11. The sanitary napkin according to claim 1 wherein the primary absorbent member further comprises a resilient member which is capable of resisting collapse and permanent deformation under normal wearing conditions of sanitary napkins during use.

12. The sanitary napkin according to claim 11 wherein the resilient member is formed from a material selected from the group consisting of nylon, polypropylene, polyurethane, polyethylene, polyester, synthetic rubber, synthetic formed films, natural rubber, sponge, and combinations thereof.

13. The sanitary napkin according to claim 1 wherein the topsheet of the primary absorbent member is an apertured film and the topsheet of secondary absorbent member is a nonwoven fabric.

14. The sanitary napkin according to claim 1 wherein the compound napkin has two flexible side flaps adjacent to and extending laterally outward from the side edges of the secondary absorbent member, the flaps being adapted to be folded over the edges of the wearer's undergarment in the crotch region in use, each flap having a proximal end that is coincident with the longitudinal side edges of the secondary absorbent member and a freely extending distal end opposite the proximal end.

15. The sanitary napkin according to claim 14 wherein the flaps are provided with attachment means on a garment-facing surface thereof.

16. The sanitary napkin according to claim 14 wherein the flaps are comprised of a laminate of integral and contiguous extensions of the topsheet and barrier sheet of the secondary absorbent member.

17. The sanitary napkin according to claim 14 wherein the flaps are folded over the topsheet the secondary absorbent member prior to being worn by the user of the napkin and releasably maintained in the folded position by a strip of release paper that extends from one flap across the topsheet of the compound napkin to the opposite flap and is releasably affixed to an adhesive on a garment facing side of the flaps.

18. The sanitary napkin according to claim 14 wherein the primary absorbent member is affixed to the liquid pervious topsheet of the secondary absorbent member along union means and the flaps are folded over the topsheet of the secondary absorbent member and the distal ends of the flaps are inserted between the primary absorbent member and the secondary absorbent member in the region intermediate the union means and the longitudinal side edge of the primary absorbent member.

19. The sanitary napkin according to claim 1, wherein the absorbent element has a width of from about 5 cm to 15 cm.

20. The sanitary napkin according to claim 1, wherein the absorbent element has a width of from about 5 to 10 cm.

21. The sanitary napkin according to claim 1, wherein the absorbent element has a width of from about 5 to 8 cm.

22. A compound sanitary napkin adapted to be worn by a user in a crotch portion of an undergarment comprising:

an uppermost primary absorbent member and a lowermost secondary absorbent member;

the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent core between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member has a contoured shape in the form of a continuous taper wherein a first transverse end region has a relatively wider width than any other portion of the primary absorbent member and the width of the primary absorbent member substantially continuously decreases from the first transverse end region to the opposite transverse end region.

23. The sanitary napkin according to claim 22 wherein the primary absorbent member has a tapered end region adapted to comfortably fit in a user's gluteal crease.

24. A compound sanitary napkin adapted to be worn by a user in a crotch portion of an undergarment comprising:

an uppermost primary absorbent member and a lowermost secondary absorbent member; the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent element between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member has dog-bone shape wherein the narrower center region has substantially parallel straight sides.

25. A compound sanitary napkin adapted to be worn by a user in a crotch portion of an undergarment comprising:

an uppermost primary absorbent member and a lowermost secondary absorbent member;

the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent core between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member and the secondary absorbent member have a combined caliper greater than 5 mm and wherein the width of the primary absorbent member in the center region is from about 10 mm to 40 mm.

26. A compound sanitary napkin adapted to be worn by a user in a crotch portion of an undergarment comprising:

an uppermost primary absorbent member and a lowermost secondary absorbent member;

the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent core between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member and the secondary absorbent member have a combined caliper of less than 5 mm and wherein the width of the primary absorbent member in the center region is from about 10 mm to about 40 mm.

27. A compound sanitary napkin adapted to be worn by a user in a crotch portion of an undergarment comprising:

an uppermost primary absorbent member and a lowermost secondary absorbent member;

the primary absorbent member including a body-facing liquid pervious topsheet, a garment facing backsheet and an absorbent core between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent element between the topsheet and the barrier sheet, the barrier sheet being joined to the topsheet around a peripheral edge portion thereof, the secondary absorbent member; and the primary absorbent member being affixed to at least a portion of the liquid pervious topsheet of the secondary absorbent member and wherein the primary absorbent member is affixed to the liquid pervious topsheet of the secondary absorbent member along union means, wherein the union means has a width that is less than the width of the primary absorbent member in a central region of the primary absorbent member and the union means has a width that is substantially the same as the width of the primary absorbent member in the transverse end regions.

28. A compound sanitary napkin adapted to be placed in a crotch portion of an undergarment and to be worn in a groin region of a female user, the compound sanitary napkin comprising:

an uppermost primary absorbent member and a lowermost secondary absorbent member;

the primary absorbent member including a body-facing liquid pervious topsheet, a garment facing backsheet and an absorbent structure between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width, wherein the width of the center region is less than the width of the first transverse end;

the secondary absorbent member including a body-facing liquid pervious topsheet, a garment-facing liquid impervious barrier sheet and an absorbent element between the topsheet and the barrier sheet, the barrier sheet being joined to the topsheet around a peripheral edge portion thereof, the primary absorbent member being affixed to at least a portion of the liquid pervious topsheet of the secondary absorbent member and wherein the width of the center region is adapted to span the groin region of the user.

29. The compound sanitary according to claim 28 wherein the center region has a width and caliper that is adapted to gently compress the user's labia majora in use.

30. The compound sanitary according to claim 28 wherein the width of the center region is adapted to span the groin region of the user along the entire length of the groin region.

31. A compound sanitary napkin adapted to be placed in a crotch portion of an undergarment and to be worn in a groin region of a female user, the compound sanitary napkin comprising:

an uppermost primary absorbent member and a lowermost secondary absorbent member;

the primary absorbent member including a body-facing liquid pervious topsheet, a garment facing backsheet and an absorbent structure between the topsheet and the backsheet, the primary absorbent member having a first transverse end and an opposite second transverse end defining therebetween a length and a first longitudinal side edge and an opposite second longitudinal side edge defining therebetween a width, a center region located between the first and second transverse ends, the first transverse end, the second transverse end and the center region each having a respective width;

the secondary absorbent member including a body-facing liquid pervious topsheet, a garment-facing liquid impervious barrier sheet and an absorbent element between the topsheet and the barrier sheet, the barrier sheet being joined to the topsheet around a peripheral edge portion thereof, the primary absorbent member being affixed to at least a portion of the liquid pervious topsheet of the secondary absorbent member and wherein the width of the center region is adapted to span the groin region of the user along the entire length of the groin region.

* * * * *